United States Patent
Hu et al.

(10) Patent No.: US 11,590,255 B2
(45) Date of Patent: Feb. 28, 2023

(54) RUBBER-BASED SOFT GEL SKIN ADHESIVES

(71) Applicant: Avery Dennison Corporation, Glendale, CA (US)

(72) Inventors: Xianbo Hu, Pepper Pike, OH (US); Neal Carty, Chicago, IL (US)

(73) Assignee: Avery Dennison Corporation, Glendale, CA (US)

( * ) Notice: Subject to any disclaimer, the term of this patent is extended or adjusted under 35 U.S.C. 154(b) by 0 days.

(21) Appl. No.: 16/346,655

(22) PCT Filed: Nov. 10, 2017

(86) PCT No.: PCT/US2017/061015
§ 371 (c)(1),
(2) Date: May 1, 2019

(87) PCT Pub. No.: WO2018/089742
PCT Pub. Date: May 17, 2018

(65) Prior Publication Data
US 2020/0108169 A1     Apr. 9, 2020

Related U.S. Application Data

(60) Provisional application No. 62/420,611, filed on Nov. 11, 2016.

(51) Int. Cl.
| | | |
|---|---|---|
| *A61L 15/58* | (2006.01) | |
| *A61L 15/44* | (2006.01) | |
| *A61L 24/00* | (2006.01) | |
| *A61L 24/04* | (2006.01) | |
| *C08K 5/01* | (2006.01) | |
| *C08K 5/103* | (2006.01) | |
| *C08K 5/29* | (2006.01) | |
| *C09J 125/10* | (2006.01) | |

(52) U.S. Cl.
CPC ............. *A61L 15/585* (2013.01); *A61L 15/44* (2013.01); *A61L 24/0015* (2013.01); *A61L 24/043* (2013.01); *C08K 5/01* (2013.01); *C08K 5/103* (2013.01); *C08K 5/29* (2013.01); *C09J 125/10* (2013.01); *A61L 2300/206* (2013.01)

(58) Field of Classification Search
CPC ...... A61L 15/585; A61L 15/44; A61L 24/043; A61L 24/0015; A61L 2300/206; C08L 5/01; C08L 5/103; C08L 5/29; C09J 125/10
See application file for complete search history.

(56) References Cited

U.S. PATENT DOCUMENTS

| | | | |
|---|---|---|---|
| 4,367,732 A | 1/1983 | Poulsen et al. | |
| 4,551,490 A | 11/1985 | Doyle et al. | |
| 4,833,193 A | 5/1989 | Sieverding | |
| 5,354,597 A * | 10/1994 | Capik | B32B 25/08 |
| | | | 428/152 |
| 5,559,165 A | 9/1996 | Paul | |
| 5,827,528 A * | 10/1998 | Kubo | A61L 24/043 |
| | | | 424/443 |
| 6,414,073 B1 | 7/2002 | Nakamura et al. | |
| 6,448,303 B1 | 9/2002 | Paul | |
| 6,458,886 B1 | 10/2002 | Nielsen et al. | |
| 6,849,672 B2 | 2/2005 | Mehawej et al. | |
| 7,015,155 B2 | 3/2006 | Zhou et al. | |
| 7,109,263 B2 | 9/2006 | Paul et al. | |
| 7,211,627 B2 | 5/2007 | Kawanabe | |
| 7,335,416 B2 | 2/2008 | Lipman | |
| 7,560,512 B2 | 7/2009 | DuBois | |
| 8,129,464 B2 | 3/2012 | Abba et al. | |
| 8,987,372 B2 | 3/2015 | Hu et al. | |
| 9,078,948 B2 | 7/2015 | Jensen et al. | |
| 2014/0303261 A1 * | 10/2014 | Ramjit | A61L 15/58 |
| | | | 514/770 |
| 2014/0324006 A1 | 10/2014 | Zhong | |
| 2014/0335299 A1 | 11/2014 | Wang et al. | |
| 2015/0017868 A1 | 1/2015 | Stafeil et al. | |
| 2015/0166855 A1 | 6/2015 | Lee et al. | |
| 2016/0075924 A1 | 3/2016 | Takenake et al. | |
| 2016/0152871 A1 | 6/2016 | Bieber et al. | |
| 2016/0228600 A1 * | 8/2016 | Wibaux | A01N 47/44 |
| 2016/0237324 A1 | 8/2016 | Jang et al. | |

FOREIGN PATENT DOCUMENTS

| | | |
|---|---|---|
| EP | 0443263 | 8/1991 |
| EP | 2241340 | 10/2010 |
| WO | 98/28023 | 7/1998 |
| WO | 99/13016 | 3/1999 |
| WO | 2016077132 | 5/2016 |

OTHER PUBLICATIONS

International Search Report & Written Opinion issued in corresponding IA No. PCT/US2017/061015 dated Feb. 19, 2018.
International Preliminary Report on Patentability dated May 23, 2019 issued in corresponding IA No. PCT/US2017/061015 filed Nov. 10, 2017.

\* cited by examiner

*Primary Examiner* — Shirley V Gembeh

(57) ABSTRACT

Adhesives comprising rubber, tackifier, oil, and optionally absorbent and active ingredient are described. The adhesives are suitable for medical applications as they are repositionable on skin. Also described are medical articles using the adhesives.

10 Claims, 21 Drawing Sheets

RUBBER-BASED SOFT GEL SKIN ADHESIVES

The present application is a 371 of International Application No. PCT/US17/61015, which was published in English on May 17, 2018, and claims the benefit of U.S. Provisional Patent Application No. 62/420,611 filed Nov. 11, 2016, both of which are incorporated herein by reference in their entireties.

FIELD

The present subject matter relates to rubber-based skin adhesives.

BACKGROUND

Many medical adhesives are based on silicone soft gel adhesives. Although satisfactory in many respects, such silicone adhesives cannot be sterilized using certain techniques such as by exposure to gamma radiation. In addition, most if not all silicone adhesives for medical use exhibit low breathability. Thus, apertures or other physical transport passageways must typically be formed in regions or layers of silicone adhesive. Silicone adhesives are formed from a two-part reactive system and once mixed, react to form the adhesive which limits subsequent processing.

Accordingly, new adhesives that address and ideally overcome the various limitations are desired.

SUMMARY

The difficulties and drawbacks associated with previous approaches are addressed in the present subject matter as follows.

In one aspect, the present subject matter provides a rubber-based skin adhesive comprising at least one rubber component, at least one tackifier, and at least one oil. The adhesive may exhibit a soft, gel-like consistency (also referred to herein as a "soft gel") and may be repositionable on skin. As used herein, the terms "soft, gel-like consistency" and "soft gel" refer to an adhesive that is may be a solid jelly-like material. As used herein for the "soft" portion of the "soft, gel-like consistency" or "soft gel" adhesive, the adhesive may provide both an effective barrier for a patient and a comfortable adhesive for fragile or delicate skin. Also as used herein, the term "repositionable" means an adhesive that may be removed and reapplied with at least some adhesion. Also with a "repositionable" adhesive, the adhesive may be removed such that it comes lightly off the skin and provides less painful removal of the adhesive.

In another aspect, the present subject matter provides an adhesive assembly comprising a medical article having an exterior surface, and a region of adhesive disposed on the exterior surface of the medical article. The adhesive includes (i) at least one rubber component, (ii) at least one tackifier, and (iii) at least one oil, wherein the adhesive exhibits a soft, gel-like consistency and is repositionable on skin.

As will be realized, the subject matter described herein is capable of other and different embodiments and its several details are capable of modifications in various respects, all without departing from the claimed subject matter. Accordingly, the drawings and description are to be regarded as illustrative and not restrictive.

DETAILED DESCRIPTION OF THE EMBODIMENTS

Figure 1:
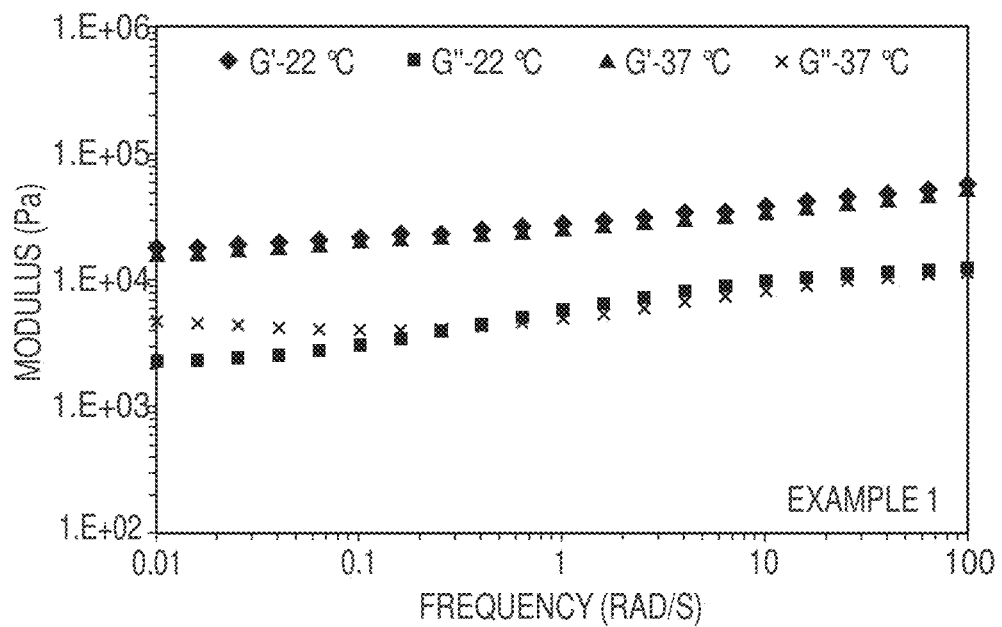
FIG. 1 is a graph of modulus as frequency changes of the sample of Example 1.

The present subject matter provides adhesive formulations based on rubber, tackifier, and oil that exhibit a soft, gel-like consistency to enable gentle removal from the skin as well as repositionability, i.e., the adhesive can be applied to the skin, removed, and then re-applied multiple times. Optionally, the adhesive can be formulated to provide moisture management capabilities by incorporating absorbent material. Optionally, the adhesive can be formulated to provide additional functions by incorporating at least one active ingredient.

In particular embodiments, the adhesive may comprise styrene-isoprene-styrene (SIS) block copolymer, oil, and tackifier. The materials are combined in proportions that result in a soft, gel-like consistency with rheology that in many embodiments is similar but not identical to, soft silicone gel pressure sensitive adhesives (PSA) known in the industry. As a result, the adhesive is sufficiently tacky to provide good bonding to skin, but the adhesive can be peeled off from the skin gently with little or no pain or trauma. And after the adhesive has been removed, the adhesive can be re-applied again with at least some adhesion to the skin. In certain embodiments, the adhesives include hydrophilic or absorbent particles (here referred to as absorbent in present subject matter), e.g., carboxymethylcellulose, dispersed within the adhesive to impart fluid-handling capabilities. When hydrophilic or absorbent particle is added, the adhesive gains the ability to either allow moisture vapor to move through the adhesive, i.e., breathability or to absorb fluid and also allow moisture vapor to move through the adhesive. The adhesive can be processed from a solvent solution or as a hot melt. In many embodiments, the adhesive may be a pressure sensitive adhesive.

Generally, the adhesives of the present subject matter comprise (i) at least one rubber component, (ii) at least one tackifier, and (iii) at least one oil where the adhesive exhibits a soft gel-like consistency and is repositionable on the skin. In other embodiments, the adhesive can optionally include (iv) at least one absorbent. The absorbent may provide moisture management functions. In some embodiments, at least one absorbent may comprise carboxymethyl cellulose. In still additional embodiments, the adhesive can optionally include (v) at least one active ingredient, instead of or in further combination with the absorbent(s), i.e., (iv). In some embodiments, the rubber component may include a SIS block copolymer. However, a wide array of rubber components can be used, as described below. The resulting adhesive described herein exhibits a soft, gel-like consistency with a rheology similar to soft silicone gel PSAs.

Table 1a set forth below lists some example weight proportions of components for adhesives of the present subject matter which do not include absorbents, i.e., are "absorbent free."

TABLE 1a

Proportions of Components of Absorbent Free Adhesives

| Component | Formula 1 (wt %) | Formula 2 (wt %) |
|---|---|---|
| Rubber | 10-55 | 20-25 |
| Tackifier | 15-50 | 25-35 |
| Oil | 20-70 | 30-50 |

Table 1b set forth below lists some example weight proportions of components for adhesives which include at least one absorbent.

TABLE 1b

Proportions of Components of Adhesives Containing at Least One Absorbent

| Component | Formula 3 (wt %) | Formula 4 (wt %) |
|---|---|---|
| Rubber | 7-33 | 15-20 |
| Tackifier | 15-45 | 20-35 |

TABLE 1b-continued

Proportions of Components of Adhesives Containing at Least One Absorbent

| Component | Formula 3 (wt %) | Formula 4 (wt %) |
|---|---|---|
| Oil | 15-60 | 20-45 |
| Absorbent | 10-40 | 20-35 |

Rubber Component(s)

A wide array of rubber component(s) can be used in the adhesives of the present subject matter. The weight proportion of the rubber component(s) where no absorbents are added may be about 10% to about 55%. In some embodiments, the weight proportion of the rubber component(s) where no absorbents are added may be about 20% to about 25%. The weight proportion of the rubber component(s) where at least one absorbent is added may be about 7% to about 33%. In some embodiments, the weight proportion of the rubber component(s) where at least one absorbent is added may be about 15% to about 20%.

As previously noted, in many embodiments, at least one rubber component is a synthetic rubber. Generally, any linear or radial A-B-A and/or A-B block copolymers or branched block copolymer(s) which are based on styrene-butadiene (SB), styrene-isoprene (SI), and/or hydrogenated styrene-diene copolymers such as styrene ethylene-butylene can be used as at least one rubber component. Combinations of these components can also be used. In some embodiments, suitable styrene-diene copolymers are exemplified by a blend of linear styrene-isoprene-styrene triblock copolymer and linear styrene-isoprene diblock copolymer. Such a material is available from Kraton Polymers as KRATON® D-1161K or KRATON® D-1161P and has a bound styrene content of about 15% and a diblock content of about 19%. In many embodiments, at least one rubber component includes SIS block copolymer(s). In other embodiments, at least one rubber component includes styrene-butadiene-styrene (SBS) block copolymers. In many embodiments, at least one rubber component includes olefin block copolymer (OBC). Such a material is available from Dow Chemical Company under the designation INFUSE™ or similar products from the same using INSITE™ catalyst technology.

Tackifier(s)

The tackifier(s) used in the present subject matter adhesives are compatible, or at least substantially compatible, with the rubber component(s) also utilized in the adhesives. The weight proportion of the tackifier component(s) where no absorbents are added may be about 15% to about 50%. In some embodiments, the weight proportion of the tackifier component(s) where no absorbents are added may be about 25% to about 35%. The weight proportion of the tackifier component(s) where at least one absorbent is added may be about 15% to about 45%. In some embodiments, the weight proportion of the tackifier component(s) where at least one absorbent is added may be about 20% to about 35%.

A wide variety of tackifiers can be used to enhance the tack and peel of the adhesive and can be used singularly or in combination. These include, but are not limited to, rosins and rosin derivatives including rosinous materials that occur naturally in the oleoresin of pine trees, as well as derivatives thereof including rosin esters, modified rosins such as fractionated, hydrogenated, dehydrogenated, and polymerized rosins, modified rosin esters and the like.

For the tackifiers, there may also be employed terpene resins which are hydrocarbons of the formula $C_{10}H_{16}$, occurring in most essential oils and oleoresins of plants, and phenol modified terpene resins like alpha pinene, beta pinene, dipentene, limonene, myrecene, bornylene, camphene, and the like. Various aliphatic hydrocarbon resins like Escorez 1304, manufactured by Exxon Chemical Co., and aromatic hydrocarbon resins based on $C_9$, $C_5$, dicyclopentadiene, coumarone, indene, styrene, substituted styrenes and styrene derivatives and the like can also be used.

In many embodiments, at least one tackifier includes hydrogenated and partially hydrogenated resins such as Regalrez 1018, Regalrez 1033, Regalrez 1078, Regalrez 1094, Regalrez 1126, Regalrez 3102, Regalrez 6108, etc., produced by Eastman Chemical Company. In some embodiments, at least one tackifier includes various terpene phenolic resins of the type SP 560 and SP 553, manufactured and sold by Schenectady Chemical Inc., Nirez 1100, manufactured and sold by Reichold Chemical Inc., and Piccolyte S-100, manufactured and sold by Hercules Corporation. In other embodiments, at least one tackifier includes various mixed aliphatic and aromatic resins, such as Hercotex AD 1100, manufactured and sold by Hercules Corporation.

In many embodiments, at least one tackifier includes a hydrogenated pentaerythritol rosin ester, for example HYDROGRAL P commercially available from DRT (Dérivés Résiniques et Terpéniques).

In certain embodiments, at least one tackifier includes one or more hydrogenated hydrocarbon resins such as those commercially available from Arakawa under the designations ARKON P-115 and ARKON P-125.

In still additional embodiments, at least one tackifier includes styrenated terpene resins such as DERCOLYTE TS105 from DRT.

The particular tackifying resin and/or amount selected for a given formulation may depend upon the type of rubber polymer being tackified. Many resins which are known in the prior art for tackifying acrylic based pressure sensitive adhesives can be effectively used in the practice of the present subject matter, although the scope of the present subject matter is not limited to only such resins. Resins described in Satas, Handbook of Pressure Sensitive Adhesive Technology, Von Nostrand Reinhold, Co, Chap. 20, pages 527-584 (1989) (incorporated by reference herein) can potentially be used.

Oil(s)

The term "oil", as used herein refers to oils from mineral sources and can be a mixture of linear, branched and aromatic hydrocarbons, paraffins, and waxes. The weight proportion of the oil component(s) where no absorbents are added may be about 20% to about 70%. In some embodiments, the weight proportion of the oil component(s) where no absorbents are added may be about 30% to about 50%. The weight proportion of the oil component(s) where at least one absorbent is added may be about 15% to about 60%. In some embodiments, the weight proportion of the oil component(s) where at least one absorbent is added may be about 20% to about 45%.

In some embodiments, at least one oil may be derived from petroleum distillate, which may be divided into three classes: paraffinic oil, based on n-alkanes; naphthenic oil, based on cycloalkanes; and aromatic oils, based on aromatic hydrocarbons.

A variety of different types and/or grades of oil can be used in the adhesives of the present subject matter. In many embodiments, at least one oil component is a USP White Mineral Oil. In some embodiments, USP White Mineral Oil may be a low viscosity (approximately 25 cSt at about 40° C.) hydrocarbon oil that does not readily evaporate at room temperature or at elevated temperature, so that at least one oil component can withstand high-temperature drying or hot melt processing of the adhesive, e.g., exposure to temperatures up to about 150° C.

Additional nonlimiting examples of suitable mineral oils that can be utilized in the present subject matter adhesives include those that are commercially available from Petro Canada under the designations PURETOL 10, PURETOL 13, and PURETOL 19 up to Puretol 55.

Additional nonlimiting examples of at least one oil that can be utilized in the present subject matter adhesives include those liquid polymers or oligomers such as synthetic rubbers that are commercially available from Kuraray's LIR, LSR, and L-SBR series, Royal Elastomer's Isolene or Kalene series, Kraton's liquid IR rubber series, polybutylene or polyisobutylene (PIB) from TPC Group's TPC5xxx and TPC1xxx series product, from BASF's Oppanol, and Exxon's Vistanes, or those from Crescent Chemicals. In some embodiments, at least one oil may comprise one or more liquid isoprene rubber(s), liquid butadiene rubbers, liquid polyisobutylene(s), and combinations thereof. In many embodiments, at least one can be either combined with one or more other oil(s) described herein or used exclusively to provide softness, tack and increase stability of the resulting rubber-based skin adhesive.

Absorbent(s)

Similarly, a wide array of absorbents can be utilized in the adhesive compositions according to the present subject matter. The weight proportion of the absorbent(s) may be about 10% to about 40%. In some embodiments, the weight proportion of the absorbent(s) may be about 30%. Table 2 below provides some weight ranges for some example formulas for adhesives which include at least one absorbent compared to formulas without an absorbent.

TABLE 2

Comparison of Proportions of Components of Adhesives Containing at Least One Absorbent

|  |  | No Absorbent | With Absorbent |
|---|---|---|---|
| Rubber | Formula A | 10-55 | 7-33 |
|  | Formula B | 20-25 | 15-20 |
| Tackifier | Formula A | 15-50 | 15-45 |
|  | Formula B | 25-35 | 20-35 |
| Oil | Formula A | 20-70 | 15-60 |
|  | Formula B | 30-50 | 20-45 |
| Absorbent | Formula A |  | 10-40 |
|  | Formula B |  | 20-35 |

In many embodiments, at least one absorbent includes one or more hydrophilic polymers that are soluble or insoluble but either swellable or non-swellable in water, as the moisture-absorbing component. In many embodiments, the moisture absorbing agents may include at least one hydrocolloid and/or at least one super absorbent polymer.

The adhesive composition may include one or more hydrocolloids. The hydrocolloids promote and/or enable the final composition to adhere to moist body surfaces. This phenomenon is termed "wet tack". One or more water swellable hydrocolloids may also be present. The hydrocolloid may be linear or crosslinked. Suitable hydrocolloids may include, but are not limited to, hydrocolloids such as sodium carboxymethyl cellulose, and natural products such as gelatin, pectin, guar gum, locust bean gum, tragacanth gum, gum karaya, starches, gum arabic, alginic acid and its sodium and/or calcium salts. In some embodiments, other hydrocolloids may include polyvinyl alcohol, polyvinyl acetate, polyvinyl pyrollidone, polyacrylic acid, polyhydroxyalkyl acrylates, polyacrylamides, high molecular weight polyethylene glycols and polypropylene glycols. Other hydrocolloids may also include crosslinked or crystalline sodium carboxymethyl cellulose, crosslinked dextran, starch-acrylonitrile graft copolymer, microcrystalline cellulose, crosscarmellose sodium and sodium starch glycolate.

Suitable insoluble swellable polymers may include crosslinked sodium carboxymethyl cellulose and crystalline sodium carboxymethyl cellulose.

For certain embodiments, one or more types or grades of carboxymethyl cellulose (CMC) in the present subject matter compositions and methods may be used. CMC is a cellulose ether comprised of repeating cellobiose units. These are composed of two anhydroglucose units (beta-glucopyranose residues). A parameter used in referring to grades of CMC is the degree of polymerization. This is the number of anhydroglucose units which are joined through 1,4 glucosidic linkages. Each anhydroglucose unit contains three hydroxyl groups. By substituting carboxymethyl groups for some of the hydrogens of the hydroxyl groups, sodium carboxymethyl cellulose is obtained. The average number of hydroxyl groups substituted per anhydroglucose unit is known as the "degree of substitution." If all three hydroxyls are replaced, the maximum theoretical degree of substitution is 3.0 (although not possible to practice).

Another parameter used in reference to CMC is average chain length or degree of polymerization. Average chain length (or the degree of polymerization) and the previously noted degree of substitution determine molecular weight of the CMC polymer.

For many embodiments, the CMC utilized in the present subject matter has a degree of substitution of from about 0.2 to about 1.5, and in other embodiments from about 0.7 to about 1.2. In particular embodiments, the degree of substitution of the CMC is from about 0.65 to about 0.90. The weight average molecular weight (Mw) of CMC may be within a range of from about 17,000 to about 700,000. The present subject matter includes CMC grades having weight average molecular weights (Mw) less than about 17,000 and greater than about 700,000.

In certain versions of the present subject matter, at least one absorbent is sodium carboxymethyl cellulose commercially available from various sources such as from Ashland Chemical under the designation AQUASORB A500 or A800. It is also contemplated that instead of, or in addition to, carboxymethyl cellulose; hydroxypropyl cellulose, hydroxypropylmethyl cellulose, and variants thereof can be used in the present subject matter.

In certain versions of the present subject matter, at least one non-swellable absorbent is crystalline cellulose including both microcrystalline cellulose such as Avicel PH series from FMC and cellulose nanocrystals (CNC) or nanocrystalline cellulose (NCC) from CelluForce and their derivatives as well.

At least one super absorbent polymer (SAP) in the adhesive compositions comprises a water-swellable, hydrogel-forming absorbent polymer capable of absorbing large quantities of liquids such as water, body fluids (e.g., urine, blood), and the like. Additionally, the SAP is capable of retaining such absorbed fluids under moderate pressures. In some embodiments, the SAP absorbs many times its own weight in water, for example at least about 50 times, particularly at least about 100 times, and more particularly at least about 150 times its weight in water. Additionally, the SAP exhibits good saline fluid absorption under load and high saline fluid absorption capacity. In some embodiments, the SAP absorbs at least about 10 times, particularly at least about 30 times, and more particularly at least about 50 times its weight in saline fluid. Even though the SAP is capable of absorbing many times its own weight in water and/or saline, it does not dissolve in these fluids.

The ability of the SAP to absorb water and/or saline fluid is related to the degree of crosslinking present in the SAP. Increasing the degree of crosslinking increases the SAP's total fluid holding capacity under load. The degree of crosslinking may be optimized for the rate and amount of absorbency in an adhesive composition. Certain SAPs are at least about 10%, more particularly from about 10% to about 50%, and more particularly from about 20% to about 40% crosslinked. Examples of suitable SAPs may include, but are not limited to, crosslinked and polymerized β-beta ethylenically unsaturated mono- and dicarboxyiic acids and acid anhydride monomers including, e.g., acrylic acid, methacrylic acid, crotonic acid, maleic acid/anhydride, itaconic acid, fumaric acid, and combinations thereof.

At least one super absorbent polymer in the present subject matter may include crosslinked acrylate polymers, crosslinked products of vinyl alcohol-acrylate copolymers, crosslinked products of polyvinyl alcohols grafted with maleic anhydride, crosslinked products of acrylate-methacrylate copolymers, crosslinked saponification products of methyl acrylate-vinyl acetate copolymers, crosslinked products of starch acrylate graft copolymers, crosslinked saponification products of starch acrylonitrile graft copolymers, crosslinked products of carboxymethyl cellulose polymers and crosslinked products of isobutylene-maleic anhydride copolymers, and combinations thereof.

In some embodiments, the super absorbent polymer(s) is in the form of particles and generally are spherical and have an average particle size of from about 1 micrometer (μm) to about 400 μm. Particularly the particles have an average particle size of from about 20 μm to about 200 μm, and more particularly from about 20 μm to about 150 μm. In one embodiment, the particle size of the particles is less than about 150 μm, or less than about 100 μm. At least one commercially available super absorbent particles may include, e.g., sodium polyacrylate super absorbent particles available under the AQUA KEEP series of trade designations including, e.g., particles having an average particle size of from about 20 μm to about 30 μm available under the trade designation AQUA KEEP 10SH-NF, particles having an average particle size of from about 200 μm to about 300 μm available under the trade designation AQUA KEEP 10SH-P, particles having an average particle size of from about 320 μm to about 370 μm available under the trade designation AQUA KEEP SA605, particles having an average particle size of from about 350 μm to about 390 μm available under the trade designations AQUA KEEP SA60SX, SA55SX n and SA 60SL I, and particles having an average particle size of from about 250 μm to about 350 μm available under the trade designation AQUA KEEP SA60N TYPE II from Sumitomo Seika Chemicals Col, Ltd. (Japan). Also available are the super absorbent materials Luquasorb 1010 and Luquasorb 1030 from BASF, Ludwigshafen, Germany Active Ingredients In certain embodiments, the adhesives may include at least one active ingredient (also referred to herein as active agents and antimicrobial agents). In some embodiments, the active ingredients are antimicrobial agents or agents for inhibiting microbial growth. The present subject matter adhesives may also comprise one or more agents that enhance antimicrobial efficacy. In these versions of the present subject matter, the adhesives can be referred to as antimicrobial adhesives. As used herein, the terms "antimicrobial" and "inhibiting microbial growth" describe the killing of, as well as the inhibition of or control of, the growth of bacteria, yeasts, fungi, and algae. "Enhancement of antimicrobial efficacy" refers to increasing the rate of kill and/or decreasing the amount of necessary antimicrobial agent to achieve antimicrobial control. The term "antimicrobial adhesive" means an adhesive that inhibits or decreases microbial growth by more than about 2 log after contact, in certain versions of the present subject matter, more than about 2 log after 24 hours, and in particular versions of the present subject matter, more than about 2 log for a time period of 7 days at use concentrations of antimicrobial agent(s) of about 0.01% to about 15% by weight. In certain versions of the present subject matter, the adhesive compositions inhibit or decrease microbial growth by more than about 3 log after 3 days, and in particular versions of the subject matter, more than about 3 log for a time period of 7 days, at use concentrations of one or more antimicrobial agents of about 0.01% to about 15% by weight. The term "antimicrobial adhesive" also refers to the noted adhesives that inhibit or decrease microbial growth by more than about 3 log, more particularly more than about 3.5 log, and more particularly more than about 6 log for the noted time periods. In particular versions of the present subject matter, the adhesive compositions may inhibit or decrease microbial growth such as vancomycin-resistant *Enterococcus faecalis* (VRE) by more than about 3.5 log and more particularly more than about 5 log after 6 hours at use concentrations of one or more antimicrobial agents of about 0.01% to about 15% by weight. In certain embodiments, the antimicrobial agent(s) are present in the adhesive compositions within a concentration range of from about 0.5% to about 5% by weight.

Non-limiting examples of antimicrobial agents include diiodomethyl-para-tolylsulfone (DIMTS, Amical®), orthophenylphenol (OPP), sodium pyrithione (NaPT), zinc pyrithione (ZPT), 3-iodo-2-propynylbutylcarbamate (IPBC), 2-methyl-4-isothiazolin-3-one (MIT), 1,2-benzisothiazolin-3-one (BIT), 2-n-octyl-4-isothiazolin-3-one (OIT), 1-(3-chloroallyl)-3,5,7-triaza-1-azoniaadamantane chloride (CTAC, Dowicil 200), 2-(4-thiazolyl)-benzimidazole (TBZ, thiabendazole), β-bromo-β-nitrostyrene (BNS), 2,4,4'-trichloro-2-hydroxyphenyl ether (Triclosan), chloroxylenol (PCMX), chlorocresol (PCMC), para-tert-amylphenol (PTAP), N-(4-chlorophenyl)-N'-(3,4-dichlorophenyl)-urea (Trichlocarban), para-hydroxybenzoic acid esters (parabens), and mixtures thereof. A partial listing of preferred antimicrobial agents includes DIMTS, OPP, NaPT, ZPT, IPBC, BIT, OIT, TBZ, BNS, 2,4,4'-trichloro-2-hydroxyphenyl ether, chloroxylenol, chlorocresol, PTAP, N-(4-chlorophenyl)-N'-(3,4-dichlorophenyl)-urea, and mixtures thereof. As described in greater detail herein, in certain embodiments at least one active ingredient is a bis-biguanide salt and particularly, chlorhexidine or a salt thereof.

At least one active agent may be non-volatile, water-soluble antimicrobial agents and may include, but are not limited to, natural components including botanical compounds such as aloe, acids such as anisic acid, hydroxy acids such as lactic acid, polypeptides such as N-cocoyl-L-arginine ethyl ether DL-pyrrolidone carboxylate CAE, enzymes such as lactoperoxidase, polysaccharides such as chitosan and proteins such as ionic lysostaphin; synthetic components including metal salts such as copper acetate and silver sulfadiazine, phenol derivatives such as phenoxyethanol, sulfur-containing compounds such as mafenide acetate, surfactants such as Nonoxynol-9, aminoglycosides such as streptomycin, iodine complexes such as povidone-iodine, hydric solvents such as benzyl alcohol, alkyl guanidines such as dodecylguanidine hydrochloride (DGH), anionic polymers such as polystyrene sulfonate, cationic polymers such as polytrimethoxysilyl propyldimethyloctadecyl ammonium chloride (AEM 5700™) and cationic nitrogen-containing organic compounds such as bis-biguanide salts and quaternary ammonium salts such as poly[(dimethylimino)-2-butene-1,4-diylchloride] and [4-tris(2-hydroxyethyl)ammonio]-2-butenyl-w-[tris(2-hydroxyethyl)ammonio]dichloride available as Polyquaternium-1. In certain embodiments, it is contemplated that in addition to the metal salts noted herein, other metal salts with antimicrobial metallic ions, for example mercury, could be used and furthermore that nonmetallic ions having antibacterial properties could also be utilized. Additional examples of other quaternary ammonium compounds which may be used as antimicrobial agents include but are not limited to Cetremide, Domiphen Bromide, polymeric quaternaries, and iodophores such as Povidone Iodine.

Bis-biguanide salts include hexamethylene biguanide hydrochloride (available as Vantocil 1139, polyhexamethylene biguanide hydrochloride (also known as PHMB, available as Cosmocil CQ®), bis-biguanide alkanes and mixtures thereof. A preferred bis-biguanide salt is 1,1'-hexamethylene bis(5-(p-chlorophenyl)biguanide salt commonly known as chlorhexidine salt. This form includes chlorhexidine diacetate, chlorhexidine dihydrochloride, chlorhexidine diphosphanilate or chlorhexidine digluconate, mainly differing by their solubility profile in various solvents and their application. In one embodiment, the chlorhexidine salt according to the present subject matter is chlorhexidine digluconate, i.e., chlorhexidine gluconate (CHG). The CHG can be present in an amount ranging from about 0.01%, and more particularly from about 0.5% to about 85% by weight of total solids, particularly from about 1.0% to about 75.0% by weight of total solids, and more particularly from about 1.0% to about 10.0% by weight of total solids. In certain embodiments, the rubber-based adhesive described herein may comprise about 3.0% of the antimicrobial agent based upon the total weight of the adhesive composition. It will be appreciated that the CHG can be present at concentrations greater than or less than any of these noted concentrations.

In one version of the present subject matter, the adhesive compositions exhibit antimicrobial efficacy against a broad spectrum of microbes. "Broad-spectrum" refers without limitation to gram-positive bacteria such as *Staphylococcus aureus* and *Enterococcus faecalis*, and gram negative bacteria such as *Escherichia coli* and *Pseudomonas aerignosa*, and clinical isolates such as methicillin-resistant *Staphylococcus aureus*(MRSA) and vancomycin-resistant *Enterococcus faecium* (VRE). The noted bacteria can often be found in a hospital environment. Additional nonlimiting examples of additional microorganisms to which the present subject matter is directed include *Staphylococcus aureus, Candida albicans, Aspergillus brasiliensis, Enterococcus faecium,* and *Staphylococcus epidermis.*

Generally, the adhesive compositions can utilize one or more antimicrobial agents in concentrations of from about 0.01% to about 15% by weight. More particularly, in certain versions of the present subject matter, the antimicrobial agent(s) are used at concentrations in a range of from about 0.1% to about 15% by weight. In some embodiments, concentrations of the antimicrobial agents may include about 1%, about 3%, and about 5% by weight for example.

It is also contemplated to use concentrations of antimicrobial agents less than about 1%, about 3%, or about 5% by weight, or other levels. However, it will be appreciated that the present subject matter includes the use of concentrations less than about 0.01% and greater than about 15% by weight.

Other Agents

There can be included in the rubber-based skin adhesive compositions described herein a wide array of additive materials. Fillers such as natural or synthetic clays, micro or nano fiber such as PET, PP, viscose, PVA, fibrils of the fibers, tackifiers, antioxidants, stabilizers, and the like may be added to the rubber-based skin adhesive. Further, pharmaceutically active components, such as for example, anti-inflammatory agents, analgesic agents, anesthetics, or other pharmaceutically acceptable compounds, which do not affect the basic properties of the rubber-based skin adhesive can be included in the adhesive in a pharmaceutically effective amount. Various pharmaceutically active agent(s) can be included in the rubber-based skin adhesive composition such as inflammatory agents, analgesic agents, anesthetics, and combinations thereof.

Glass Transition Temperatures of the Adhesive(s)

In many embodiments, adhesives of the present subject matter exhibit a glass transition temperature (Tg) within a range of from about −70° C. to about 0° C. However, it will be understood that the present subject matter includes adhesives having a Tg less than about −70° C., and/or adhesives having a Tg greater than about 0° C.

Rheology of the Adhesive(s)

As noted, in many embodiments, the adhesives of the present subject matter exhibit rheology characteristics similar to soft silicone gel PSAs. These characteristics can be quantified by reference to G' and G" properties as known in the art.

G' is also known as the storage modulus and is a measure of the energy stored and recovered per cycle of sinusoidal deformation, when different systems are compared at the same strain amplitude and rate. Adhesive compositions with a sufficiently high storage modulus for a given amount of force exhibit less deformation, and are therefore less likely to adhere to cutting blades or dies used in the converting process.

The loss modulus (G") is a measure of the energy dissipated or lost as heat or sound per cycle of sinusoidal deformation, when different systems are compared at the same strain amplitude and rate. In addition, for pressure sensitive adhesives, loss modulus can be correlated to the amount of energy dissipated in peeling the adhesive material from a substrate.

Storage modulus (G') and loss modulus (G") may be measured by placing an approximately 1.5 to 2 mm thick sample of an adhesive composition between two 8 mm parallel plates of a Rheometrics instrument (model DHR2 or DHR3 from TA Instrument or similar like model RMS-800 manufactured and sold by Rheometrics, Inc., Piscataway, N.J.), and oscillating the plates relative to one another at about 10 radians per second. The parallel plates are heated at a rate of about 1° C. per minute during the test. Measurements of the storage modulus and loss modulus, may be made at 3° C. intervals. In addition, the loss modulus and storage modulus may be measured using a similar protocol at different frequencies, as is known by those of skill in the art.

Temperature and frequency ranges of interest for the present subject matter adhesives for skin application may be about 22° C. to about 37° C. and about 0.01 rad/s to about 100 rad/s.

In many embodiments, the adhesives exhibit a storage modulus (G') at a temperature of about 22° C. to about 37° C. and a frequency of about 0.01 rad/s, of about 100 Pa to about 30,000 Pa. In other embodiments, the adhesives exhibit a storage modulus (G') at a temperature of about 22° C. to about 37° C. and a frequency of about 100 rad/s, of about 5,000 Pa to about 150,000 Pa. In other embodiments, the adhesives exhibit a loss modulus (G") at a temperature of about 22° C. to about 37° C. and a frequency of about 0.01 rad/s of about 100 Pa to about 10,000 Pa. And in other embodiments, the adhesives exhibit a loss modulus (G") at a temperature of about 22° C. to about 37° C. and a frequency of about 100 rad/s of about 1,000 to about 30,000 Pa. The adhesives of the present subject matter may exhibit one or more, or all of these properties.

Table 3 set forth below lists some example storage modulus (G') and loss modulus (G") for certain adhesives of the present subject matter.

TABLE 3

Example G' and G" Properties for Adhesives
Example Properties for Temperatures of about 22° C. to about 37° C.:

G' at 0.01 rad/s on the order of about 1,000 to about 10,000 Pa
G' at 100 rad/s on the order of about 5,000 to about 50,000 Pa
G" at 0.01 rad/s on the order of about 1,000 to about 10,000 Pa
G" at 100 rad/s on the order of about 1,000 to about 20,000 Pa Table 4 set forth below lists particular G' and G" properties for particular adhesives of the present subject matter.

TABLE 4

Particular G' and G" Properties for Adhesives
Example properties for temperatures of about 22° C. to about 37° C.:

G' at 0.01 rad/s on the order of about 500 to about 2,500 Pa
G' at 100 rad/s on the order of about 10,000 to about 50,000 Pa
G" at 0.01 rad/s on the order of about 500 to about 1,500 Pa
G" at 100 rad/s on the order of about 8,000 to about 30,000 Pa Fluid Handling Capacity of the Adhesive(s)

Fluid Handling Capacity is a measure of the combined ability of the adhesive composition to take up moisture and to evaporate such moisture to the environment. This measure may be performed by laminating a sample of the adhesive cut to the size of a Paddington cup as known in the art, to the cup on the side having the rubber ring. A circular sealing ring is placed on the sample of the cup and the screws are secured. The cup is weighed (W1). The cup is then turned upside down and filled with about 20 ml of a NaCl solution (about 0.9% wt in deionized water). A metal sealing plate is secured to the top side of the cup. The filled cup is weighed (W2). The cup is placed sample side down into an oven at about 37° C. for 24 hours. After 24 hours, the cup is removed from the oven and allowed to cool to room temperature for 30 minutes. The cup is then weighed (W3). The metal sealing plate is removed and the cup is emptied. The cup is allowed to stand for 15 minutes on a tissue to remove the NaCl solution, and then weighed (W4). The test conditions are about 23° C. (±2° C.) and about 50% (±2%) relative humidity. The Moisture Vapor Transmission Rate (MVTR) equals (W2−W3)×1,000. The Static Absorption (SA) equals (W4−W1)×1,000. The Fluid Handling Capacity (FHC) in g/10 cm²/24 hours is determined as follows:

$$FHC = (W2-W3) + (W4-W1)$$

This fluid handling capacity test is described in European Standard EN 13726.

The adhesives of the present subject matter have a broad range of FHC, may have from about 15 grams/m$^2$/day to about 5,000 grams/m$^2$/day for different medical and cosmetic applications such as "occlusive", medium or heavy exudating applications.

Adhesion of the Adhesives

The adhesion of the adhesives may be measured using a about 1"× about 8" (about 2.5 cm by about 20.3 cm) strip of the adhesive on a facestock such as film laminated on a testing panel such as a stainless steel or a HDPE (high density polyethylene) panel at 90-degree angle and a speed of about 12 inches/minute (about 30.5 cm/min). The 90-degree peel adhesion test is described in ASTM D-3330 Standard Test Method for Peel Adhesion of Pressure-Sensitive Tape and PSTC-101 Peel Adhesion Pressure Sensitive Tape.

For peel adhesion to stainless steel, the adhesive described herein may have peel adhesion of about 10 g/25.4 mm to about 2500 g/25.4 mm. In another embodiment, the peel adhesion to stainless steel may be about 50 g/25.4 mm to about 1500 g/25.4 mm. In yet another embodiment, the peel adhesion to stainless steel may be about 75 g/25.4 mm to about 1000 g/25.4 mm Reverse Tack Test The tack property of the adhesives may be measured using the reverse tack test described in ASTM D6195 Standard Test Methods for Loop Tack and PSTC-16 loop tack.

Static Shear

Static shear may be measured according to PSTC-7(Shear adhesion of pressure sensitive tape) using about 1"× about 1" (about 25.4 mm×about 25.4 mm) strip with about 500 grams weight and 5 minutes dwell time. The test panel may be stainless steel.

Repositionability

The sample for repositionability study was cut into 1×4" with a die and was done on the forearm of a participant and 12 participants in total. A Researcher wiped the area on the inner side of one of the forearms of each participant with provided alcohol wipes and allowed it to dry. The Researcher then applied 1 sample strip at a time at the pre-determined position from the randomization on the forearm of the subject in a horizontal fashion, each prototype being parallel to the other. The tape was smoothed with hand after application and peel force was measured after one-minute dwell time at an angle of 180 degrees using a peel tester (MESUR™ gauge) by the Researcher for all the participants. After the sample was peeled, it was re-applied again in the same way on the forearm at the same location as the first apply and removed one more time after a 1-minute dwell time. This process will be repeated until loss of adhesion for no more than 10 cycles. MepiTac and another commercial acrylic based PSA tape were used as controls for this example.

Adhesive Assembly in Medical Applications

The adhesives of the present subject matter can be used for adhering a wide array of articles to skin such as mammalian skin, and more particularly human skin.

Also described herein is an adhesive assembly. The adhesive assembly comprises a medical article having an exterior surface; and a region of adhesive disposed on the exterior surface of the medical article, the adhesive including (i) at least one rubber component, (ii) at least one tackifier, and (iii) at least one oil, wherein the adhesive exhibits a soft, gel-like consistency and is repositionable on skin.

The adhesive compositions described herein can be used in association with a wide array of medical articles. Non-limiting examples of such medical articles include wound dressings, surgical dressings, medical tapes, athletic tapes, surgical tapes, sensors, electrodes, ostomy appliances or related components such as sealing rings, catheters, connector fittings, catheter hubs, catheter adapters, fluid delivery tubes, electrical wires and cables, negative pressure wound therapy (NPWT) components, surgical drains, wound draining components, IV site dressings, prostheses, stoma pouches, buccal patches, transdermal patches, dentures, hairpieces, bandages, diapers, medical padding for example liposuction padding, hygiene pads, corn and callous pads, pads for cushioning and protecting blisters, toe cushioning pads, and pads for protecting and cushioning tube sites such as tracheotomy tubes.

The medical articles include one or more regions or surfaces to which the adhesive compositions of the present subject matter are applied. Forming a layer, coating, or other region of adhesive on an article enables the article to be adhered to a wide range of surfaces, including skin. It will be understood that the present subject matter is not limited to any of these articles. Instead, the subject matter includes the use of the adhesive compositions with other articles besides those noted herein. The medical articles may also include one or more layers covering the adhesive layer or coating such as a release liner.

For the adhesive of the adhesive assembly, the adhesive may include (i) at least one rubber component, (ii) at least one tackifier, and (iii) at least one oil, wherein the adhesive exhibits a soft, gel-like consistency and is repositionable on skin. The rubber component(s), tackifier(s), and oil(s) are described above in detail. The adhesive of the adhesive assembly may further include at least one absorbent, which is also further described above in detail.

In some embodiments, the weight proportion of the rubber component(s) of the adhesive assembly may be within a range of from about 10% to about 55%. In some embodiments, the weight proportion of the tackifier(s) of the adhesive assembly may be within a range of from about 15% to about 50%. In some embodiments, the weight proportion of the oil(s) of the adhesive assembly may be within a range of from about 20% to about 70%. In many embodiments, the weight proportion of the adhesive assembly may comprise: about 20% to about 25% of the rubber component(s); about 25% to about 35% of the tackifier(s); and about 30% to about 50% of the oil(s). In some embodiments, the adhesive of the adhesive assembly may further comprise at least one absorbent. In some embodiments, the weight proportion of the absorbent(s) is within a range of from about 10% to about 40%. In one embodiment, the adhesive of the adhesive assembly comprises: about 7% to about 33% of the rubber component(s); about 15% to about 45% of the tackifier(s)s; about 15% to about 60% of the oil(s); and about 10% to about 40% of the absorbent(s). In some embodiments, the weight proportion of the absorbent(s) is within a range of from about 10% to about 40%. In another embodiment, the adhesive of the adhesive assembly comprises: about 15% to about 20% of the rubber component(s); about 20% to about 35% of the tackifier(s)s; about 20% to about 45% of the oil(s); and about 20% to about 35% of the absorbent(s). In some embodiments, the adhesive of the adhesive assembly may further comprise at least one active ingredient. In some embodiments, at least one active ingredient is chlorhexidine gluconate (CHG).

In some embodiments, at least one rubber component of the adhesive assembly includes styrene-isoprene-styrene (SIS) copolymers. In some embodiments, at least one rubber component of the adhesive assembly includes styrene-butadiene-styrene (SBS) copolymers. In some embodiments, at least one rubber component of the adhesive assembly includes olefin block copolymers (OBCs). In some embodiments, at least one rubber component of the adhesive assembly includes at least one agent selected from the group comprising linear styrene-isoprene (SI) copolymers, linear styrene-butadiene (SB) copolymers, radial styrene-isoprene (SI) copolymers, radial styrene-butadiene (SB) copolymers, and combinations thereof.

In some embodiments, at least one tackifier of the adhesive assembly includes a hydrogenated pentaerythritol rosin ester. In some embodiments, at least one tackifier of the adhesive assembly includes at least one hydrogenated hydrocarbon resin. In some embodiments, at least one tackifier of the adhesive assembly includes a styrenated terpene resin. In some embodiments, at least one oil of the adhesive assembly is a USP White Mineral Oil. In some embodiments, at least one oil of the adhesive assembly includes a liquid polymer selected from the group comprising liquid isoprene rubber, liquid butadiene rubber, liquid polyisobutylene (PIB) and combinations thereof. In some embodiments, at least one absorbent of the adhesive assembly includes carboxymethyl cellulose.

In some embodiments, the adhesive of the adhesive assembly exhibits a peel adhesion on stainless steel. For peel adhesion to stainless steel, the adhesive described herein may have peel adhesion of about 10 g/25.4 mm to about 2500 g/25.4 mm. In another embodiment, the peel adhesion to stainless steel may be about 50 g/25.4 mm to about 1500 g/25.4 mm. In yet another embodiment, the peel adhesion to stainless steel may be about 75 g/25.4 mm to about 1000 g/25.4 mm In some embodiments, the adhesive of the adhesive assembly exhibits a peel adhesion on high density polyethylene (HDPE) of about 10 g/25.4 mm to about 2000 g/25.4 mm. In another embodiment, the peel adhesion on HDPE is about 50 g/25.4 mm to about 1500 g/25.4 mm. In yet another embodiment, the peel adhesion on HDPE is about 75 g/25.4 mm to about 1000 g/25.4 mm In some embodiments, the adhesive of the adhesive assembly exhibits a reverse tack of about 100 g/25.4 mm to about 3000 g/25.4 mm. In other embodiments, the reverse tack is about 200 g/25.4 mm to about 2000 g/25.4 mm. In yet other embodiments, the reverse tack is about 300 g/25.4 mm to 1000 g/25.4 mm.

In some embodiments, the adhesive of the adhesive assembly exhibits a fluid handling capacity (FHC) within a range of about 50 grams/m²/day to about 5,000 grams/m²/day.

In some embodiments, the adhesive of the adhesive assembly exhibits a storage modulus (G') at a temperature of about 22° C. to about 37° C. and a frequency of about 0.01 rad/s of about 100 Pa to about 30,000 Pa. In some embodiments, the adhesive of the adhesive assembly exhibits a storage modulus (G') at a temperature of about 22° C. to about 37° C. and a frequency of about 100 rad/s of about 5,000 Pa to about 150,000 Pa. In some embodiments, the adhesive of the adhesive assembly exhibits a loss modulus (G") at a temperature of about 22° C. to about 37° C. and a frequency of about 0.01 rad/s of about 100 Pa to about 10,000 Pa. In some embodiments, the adhesive of the adhesive assembly exhibits a loss modulus (G") at a temperature of about 22° C. to about 37° C. and a frequency of about 100 rad/s of about 1,000 Pa to about 30,000 Pa. In some embodiments, the adhesive of the adhesive assembly has a glass transition temperature within a range from about −70° C. to about 0° C.

In some embodiments, the adhesive of the adhesive assembly can be solvent coated at a temperature of less than about 77° C.

The present subject matter adhesives can be sterilized by both gamma radiation and ethylene oxide. This increases processing flexibility and applications.

The present subject matter adhesives also exhibit relatively high levels of breathability and are capable of absorbing moisture, if absorbent component(s) are utilized.

The present subject matter adhesives can be processed using solvent-based or hot melt techniques or other coating technologies. Accordingly, the adhesives and medical articles using such can be processed in a wide variety of techniques and fashions. The adhesive compositions of the present subject matter can be applied as coatings in a wide array of techniques known in the field of adhesives and medical articles. In certain embodiments, the adhesives can be solvent coated at relatively low oven temperatures such as for example less than about 77° C. (170° F.). This characteristic enables incorporation of one or more components in the adhesive, in which the component(s) may be susceptible or otherwise degrade upon exposure to high temperatures such as for example various antimicrobial agents.

The adhesive coatings or layers can be continuous, non-continuous, uniform, nonuniform or patterned. In many embodiments, coatweights of from about 10 g/m² to about 500 g/m². In some embodiments, coatweights of from about 100 g/m² to about 150 g/m² may be utilized. The adhesives can be deposited on a variety of substrates or facestocks. All different face stocks can be used including films, foams, nonwovens, scrims, fabrics made from variety of raw materials such as polymers, plastics, rubbers, metallic materials, paper, and/or combinations of these materials with others.

EXAMPLES

Adhesive samples according to the present subject matter were prepared to evaluate properties and characteristics of the resulting adhesives. Table 5 set forth below lists weight proportions of components in each of the examples described herein. Table 6 presents Moisture Vapor Transmission Rate (MVTR), Static Absorption (SA), and Fluid Handling Capacity (FHC) of Samples 4-7.

TABLE 5

Formulation of Examples

Adhesive Composition

| Sample | Oil | Tackifier | Rubber | Absorbent | Additive | Dry Weight % | | | | | |
|---|---|---|---|---|---|---|---|---|---|---|---|
| | | | | | | Oil | Tackifier | Rubber | Absorbent | Additive | Total |
| Example 1 | Oil 1 | Tackifier A | Rubber A | NA | NA | 40 | 20 | 40 | 0 | 0 | 100 |
| Example 2 | Oil 1 | Tackifier A | Rubber A | | | 50 | 25 | 25 | 0.0 | 0.0 | 100 |
| Example 3 | Oil 1 | Tackifier A | Rubber A | | | 53.33 | 26.67 | 20 | 0.0 | 0.0 | 100 |
| Example 4 | Oil 1 | Tackifier A | Rubber A | Absorbent A | | 35.00 | 17.50 | 17.5 | 30 | 0.0 | 100 |
| Example 5 | Oil 1 | Tackifier A | Rubber A | Absorbent A | | 37.33 | 18.67 | 14 | 30 | 0.0 | 100 |
| Example 6 | Oil 1 | Tackifier A | Rubber A | Absorbent A | | 36.00 | 18.00 | 16 | 30 | 0.0 | 100 |
| Example 7 | Oil 1 | Tackifier A | Rubber A | Absorbent A | | 30 | 25 | 15 | 30 | 0 | 100 |
| Example 8 | Oil 2 | Tackifier A | Rubber A | Absorbent A | | 50 | 25 | 25 | 0 | 0 | 100 |
| Example 9 | Oil 2 | Tackifier A | Rubber A | NA | NA | 45 | 30 | 25 | 0 | 0 | 100 |
| Example 10 | Oil 2 | Tackifier A | Rubber A | | | 41.67 | 33.33 | 25 | 0 | 0 | 100 |
| Example 11 | Oil 2 | Tackifier A | Rubber A | | | 37.5 | 37.5 | 25 | 0 | 0 | 100 |
| Example 12 | Oil 2 | Tackifier A | Rubber A | | | 33.33 | 41.67 | 25 | 0 | 0 | 100 |
| Example 13 | Oil 2 | Tackifier A | Rubber A | | | 30 | 45 | 25 | 0 | 0 | 100 |
| Example 14 | Oil 2 | Tackifier A | Rubber A | | | 48 | 32 | 20 | 0 | 0 | 100 |
| Example 15 | Oil 2 | Tackifier A | Rubber A | | | 40 | 40 | 20 | 0 | 0 | 100 |
| Example 16 | Oil 2 | Tackifier A | Rubber A | | | 32 | 48 | 20 | 0 | 0 | 100 |
| Example 17 | Oil 2 | Tackifier A | Rubber A | Absorbent A | | 30 | 25 | 15 | 30 | 0 | 100 |
| Example 18 | Oil 2 | Tackifier A | Rubber A | Absorbent A | | 29.17 | 23.33 | 17.50 | 30 | 0 | 100 |
| Example 19 | Oil 2 | Tackifier A | Rubber A | Absorbent B | | 29.17 | 23.33 | 17.50 | 30 | 0 | 100 |
| Example 20 | Oil 2 | Tackifier A | Rubber A | Absorbent A | | 33.60 | 22.40 | 14.00 | 30 | 0 | 100 |
| Example 21 | Oil 2 | Tackifier A | Rubber A | Absorbent B | | 33.60 | 22.40 | 14.00 | 30 | 0 | 100 |
| Example 22 | Oil 2 | Tackifier A | Rubber A | Absorbent A | | 28.00 | 28.00 | 14.00 | 30 | 0 | 100 |
| Example 23 | Oil 2 | Tackifier A | Rubber A | Absorbent A | | 22.40 | 33.60 | 14.00 | 30 | 0 | 100 |
| Example 24 | Oil 2 | Tackifier A | Rubber A | Absorbent B | | 22.40 | 33.60 | 14.00 | 30 | 0 | 100 |
| Example 25 | Oil 2 | Tackifier A | Rubber A | Absorbent A | | 30.33 | 24.27 | 15.40 | 30 | 0 | 100 |
| Example 26 | Oil 2 | Tackifier A | Rubber A | Absorbent B | | 30.33 | 24.27 | 15.40 | 30 | 0 | 100 |
| Example 27 | Oil 2 | Tackifier A | Rubber A | Absorbent B | | 36.00 | 24.00 | 15.00 | 25 | 0 | 100 |
| Example 28 | Oil 2 | Tackifier A | Rubber A | Absorbent B | | 38.40 | 25.60 | 16.00 | 20 | 0 | 100 |
| Example 29 | Oil 2 | Tackifier A | Rubber A | Absorbent B | | 40.80 | 27.20 | 17.00 | 15 | 0 | 100 |
| Example 30 | Oil 2 | Tackifier A | Rubber A | Absorbent B | | 43.20 | 28.80 | 18.00 | 10 | 0 | 100 |
| Example 31 | Oil 2 | Tackifier A | Rubber A | Absorbent A | Fiber 1 | 28.5 | 23.75 | 14.25 | 28.5 | 5 | 100 |
| Example 32 | Oil 2 | Tackifier A | Rubber A | Absorbent A | Fiber 2 | 28.5 | 23.75 | 14.25 | 28.5 | 5 | 100 |
| Example 33 | Oil 2 | Tackifier A | Rubber A | Absorbent A | Fiber 3 | 28.5 | 23.75 | 14.25 | 28.5 | 5 | 100 |
| Example 34 | Oil 2 | Tackifier A | Rubber A | Absorbent A | Fiber 4 | 28.5 | 23.75 | 14.25 | 28.5 | 5 | 100 |
| Example 35 | Oil 2 | Tackifier A | Rubber A | Absorbent A | Fiber 5 | 28.5 | 23.75 | 14.25 | 28.5 | 5 | 100 |

TABLE 6

Properties and Characteristics of Examples 4 to 7

| Sample | MVTR | SA | FHC |
|---|---|---|---|
| Example 4 | 424 | 758 | 1182 |
| Example 5 | 388 | 832 | 1220 |
| Example 6 | 1370 | 993 | 2363 |
| Example 7 | 2700 | 1293 | 3993 |

Various modulus characteristics were measured for each of Samples 1-7 and are presented in FIGS. 1-10. Several of the graphs include plots of tan delta. As known by those skilled in the art, tan delta is calculated by the ratio of loss modulus to storage modulus, i.e., G"/G'.

Figure 2:
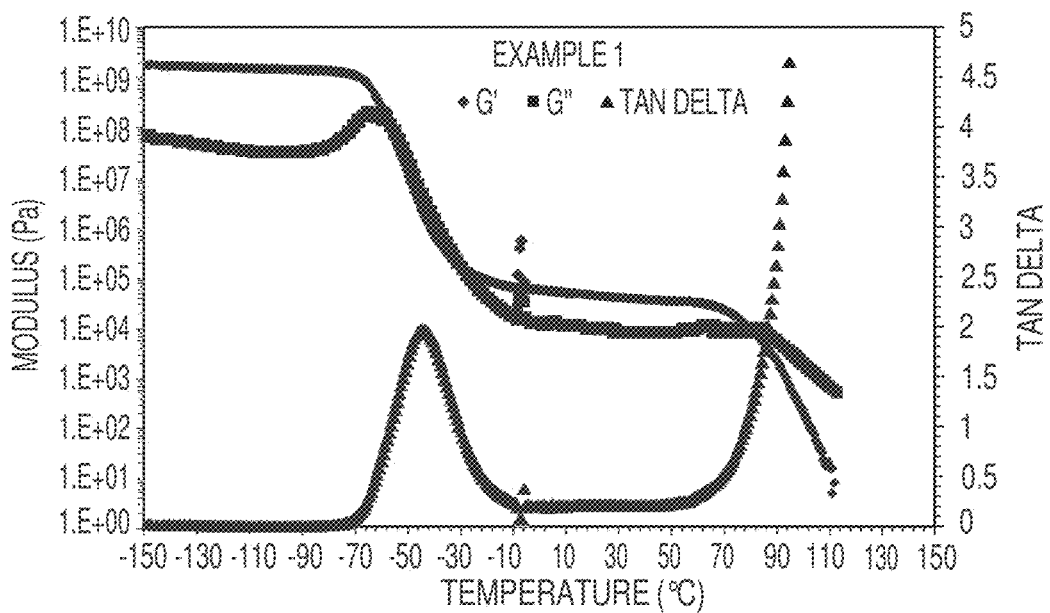
FIG. 2 is a graph of modulus and tan delta as temperature changes of the sample of Example 1.
Figure 3:
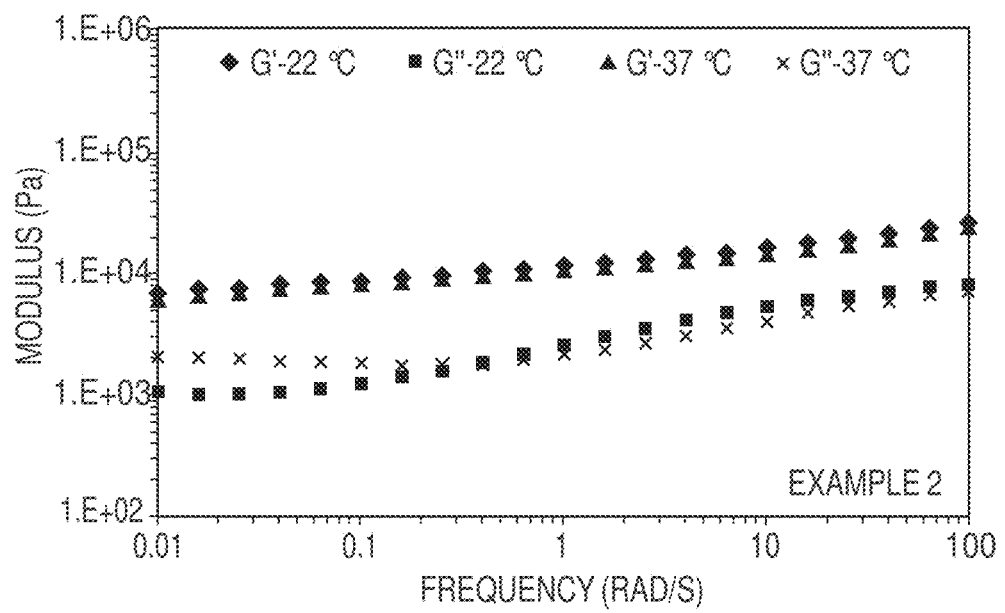
FIG. 3 is a graph of modulus as frequency changes of the sample of Example 2.
Figure 4:
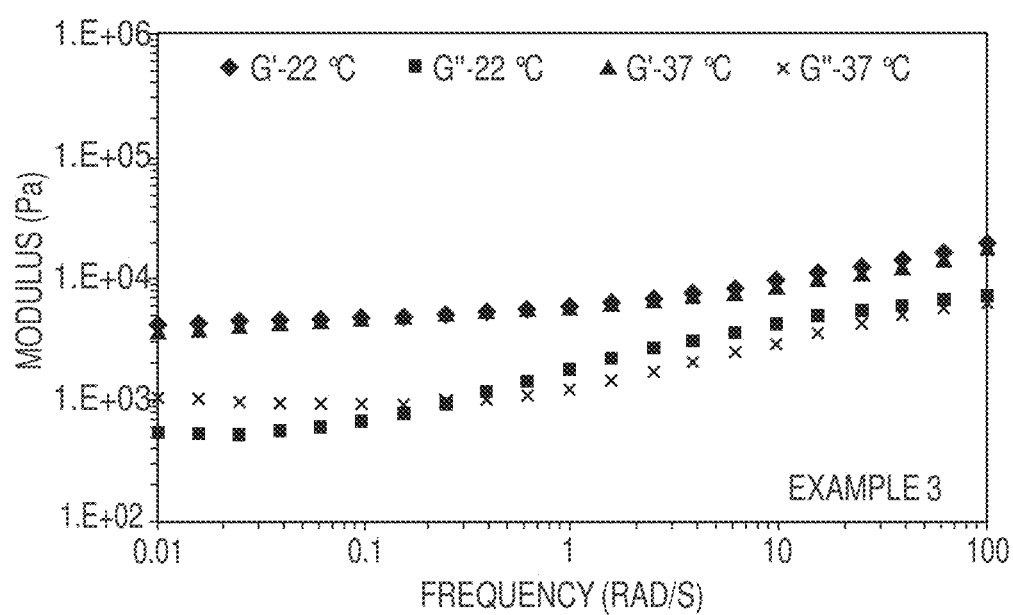
FIG. 4 is a graph of modulus as frequency changes of the sample of Example 3.
Figure 5:
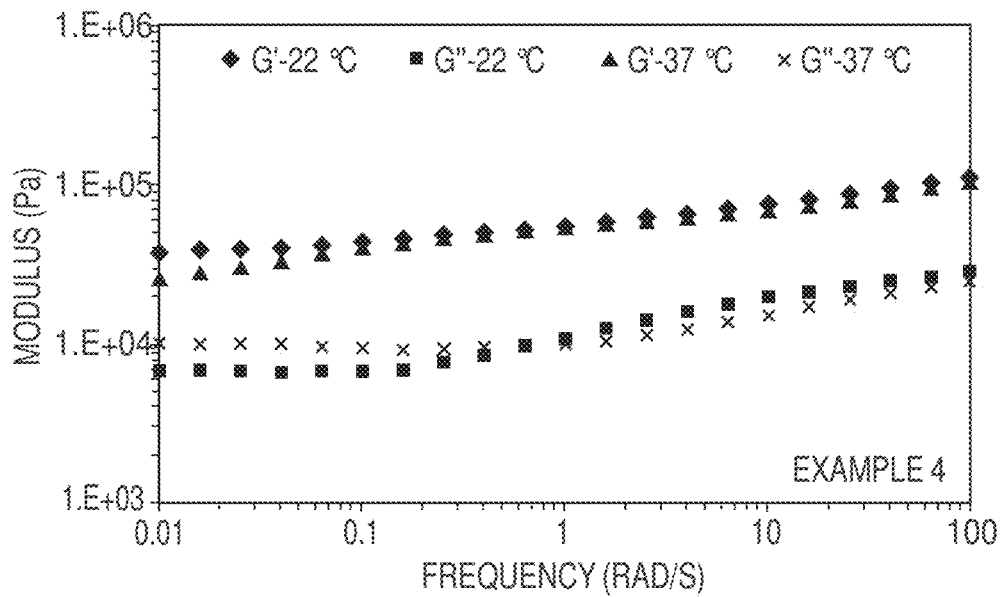
FIG. 5 is a graph of modulus as frequency changes of the sample of Example 4.
Figure 6:
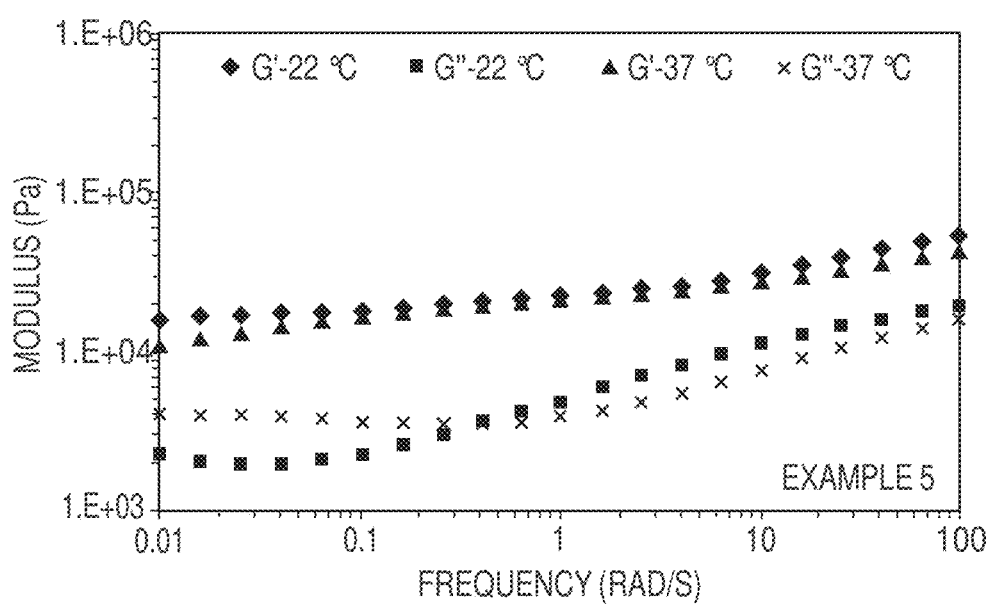
FIG. 6 is a graph of modulus as frequency changes of the sample of Example 5.
Figure 7:
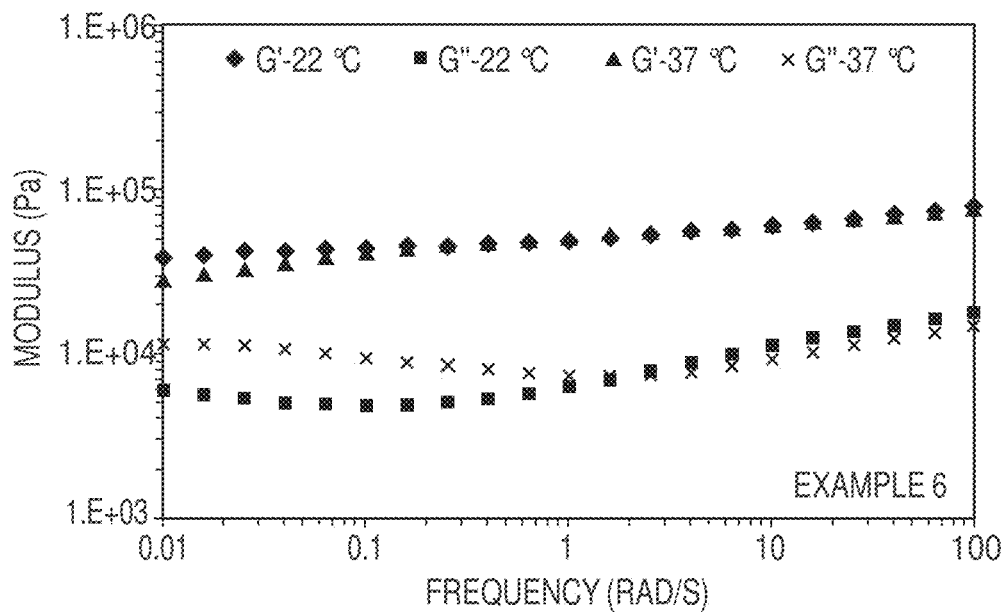
FIG. 7 is a graph of modulus as frequency changes of the sample of Example 6.
Figure 8:
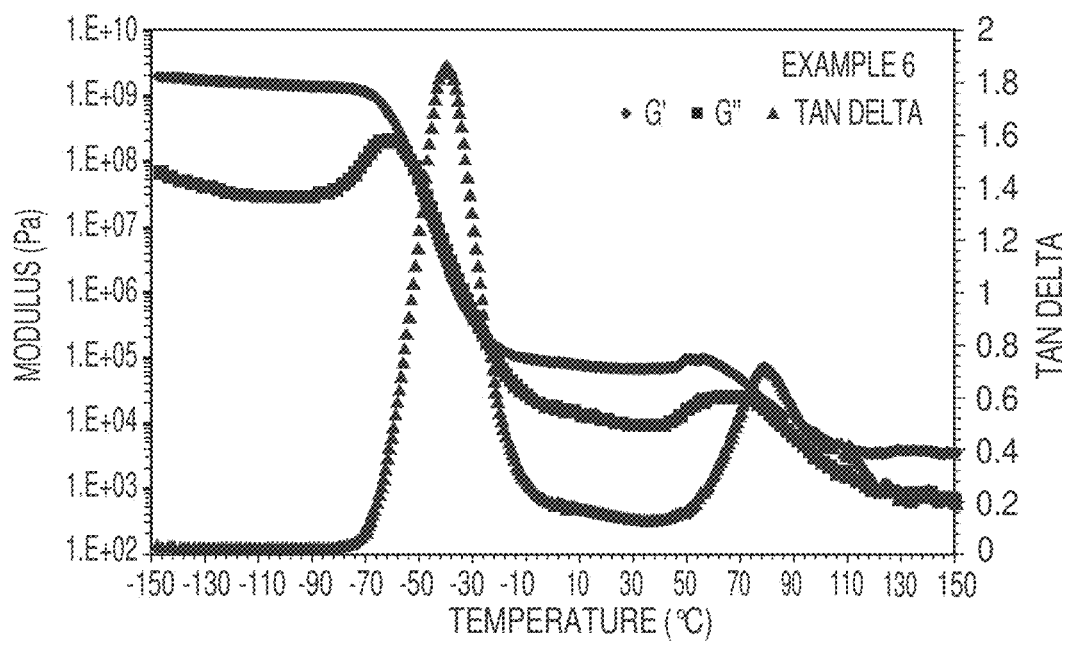
FIG. 8 is a graph of modulus and tan delta as temperature changes of the sample of Example 6.
Figure 9:
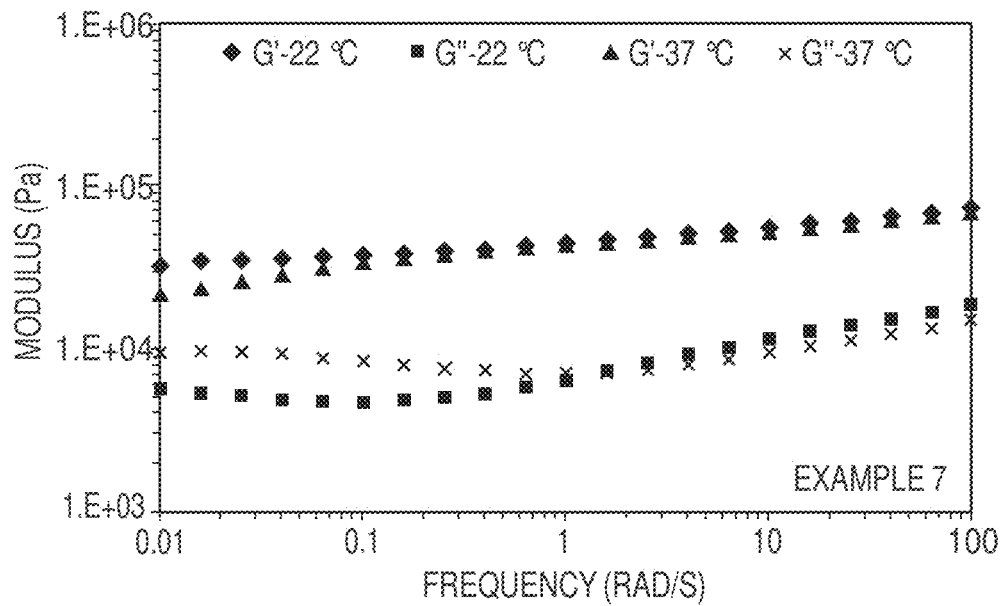
FIG. 9 is a graph of modulus as frequency changes of the sample of Example 7.
Figure 10:
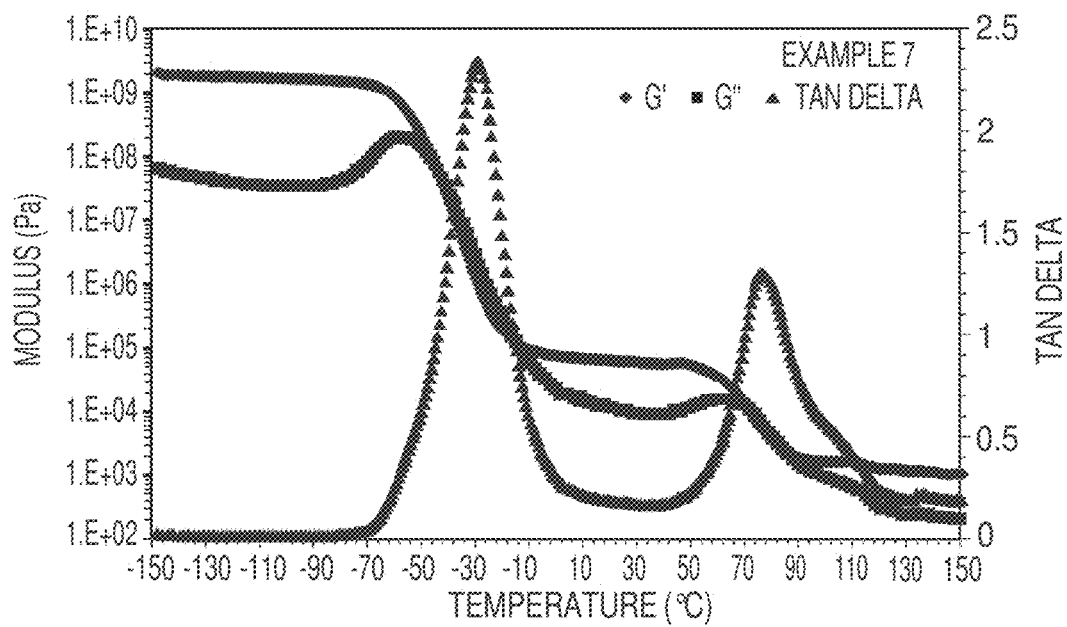
FIG. 10 is a graph of modulus and tan delta as temperature changes of the sample of Example 7.

FIG. 1 is a graph of modulus as frequency changes of the sample of Example 1. FIG. 2 is a graph of modulus and tan delta as temperature changes of the sample of Example 1. FIG. 3 is a graph of modulus as frequency changes of the sample of Example 2. FIG. 4 is a graph of modulus as frequency changes of the sample of Example 3. FIG. 5 is a graph of modulus as frequency changes of the sample of Example 4. FIG. 6 is a graph of modulus as frequency changes of the sample of Example 5. FIG. 7 is a graph of modulus as frequency changes of the sample of Example 6. FIG. 8 is a graph of modulus and tan delta as temperature changes of the sample of Example 6. FIG. 9 is a graph of modulus as frequency changes of the sample of Example 7. FIG. 10 is a graph of modulus and tan delta as temperature changes of the sample of Example 7.

These figures show that the storage and loss modulus of the samples are very similar to those of soft silicone gel at temperatures of from about 22° C. to about 37° C. as measured at a frequency range from about 0.01 to about 100 rad/s. These properties indicate that the adhesives of the present subject matter have good tack and sufficient adhesion to skin for the applications described herein, cause little to no pain in removal of the adhesives from skin, and are also repositionable.

Figure 11:
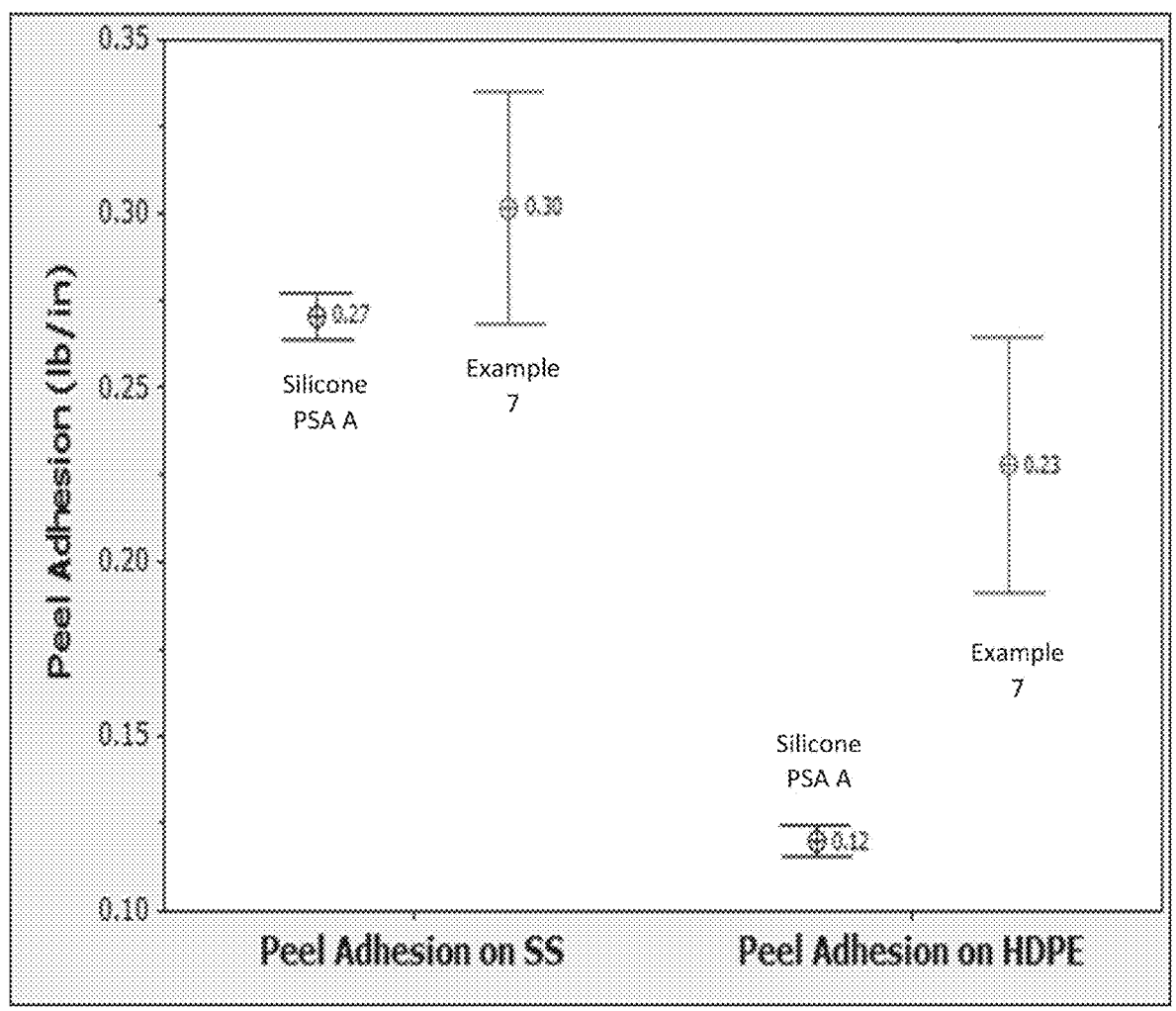
FIG. 11 is a graph of peel adhesion on Stainless steel and HDPE of MepiTac silicone PSA and Example 7.
Figure 12:
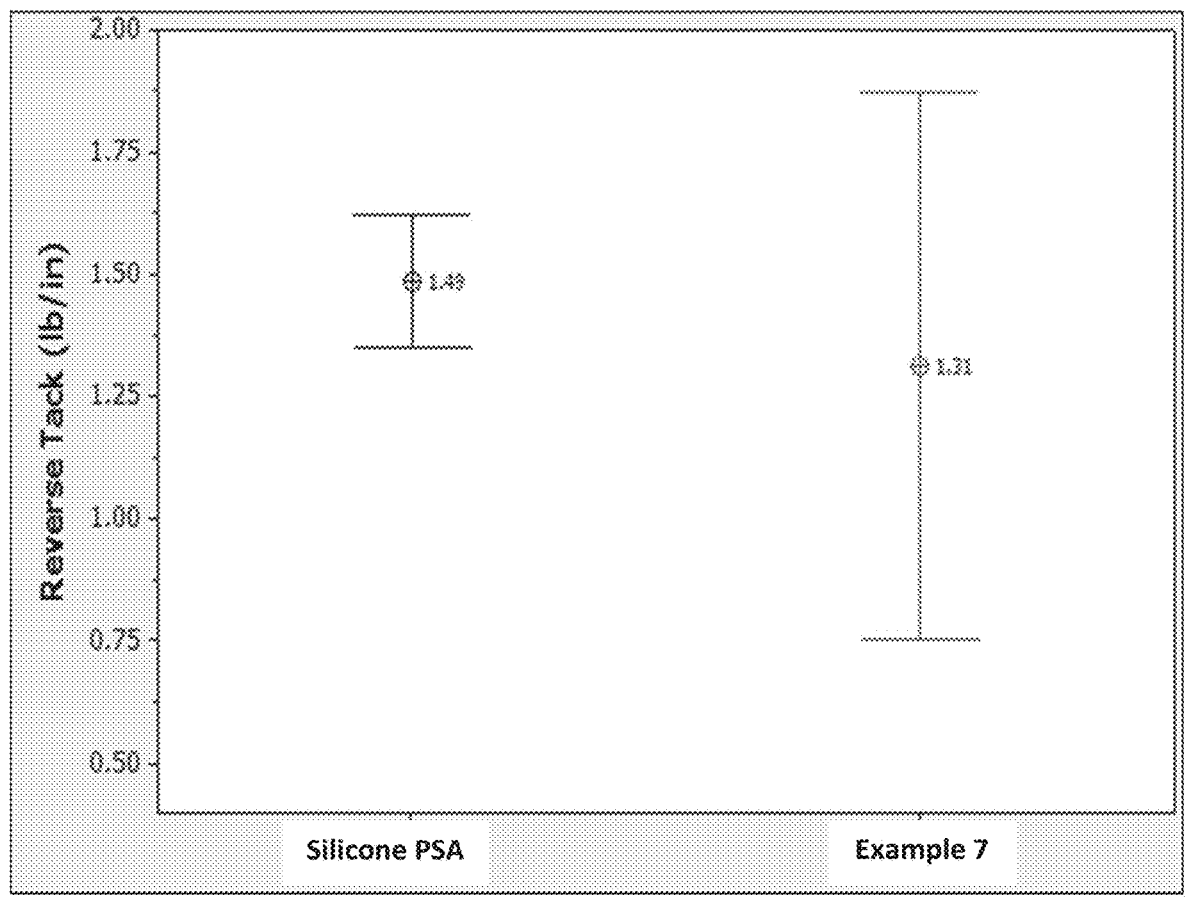
FIG. 12 is a graph of reverse tack of MepiTac silicone PSA and Example 7.
Figure 13:
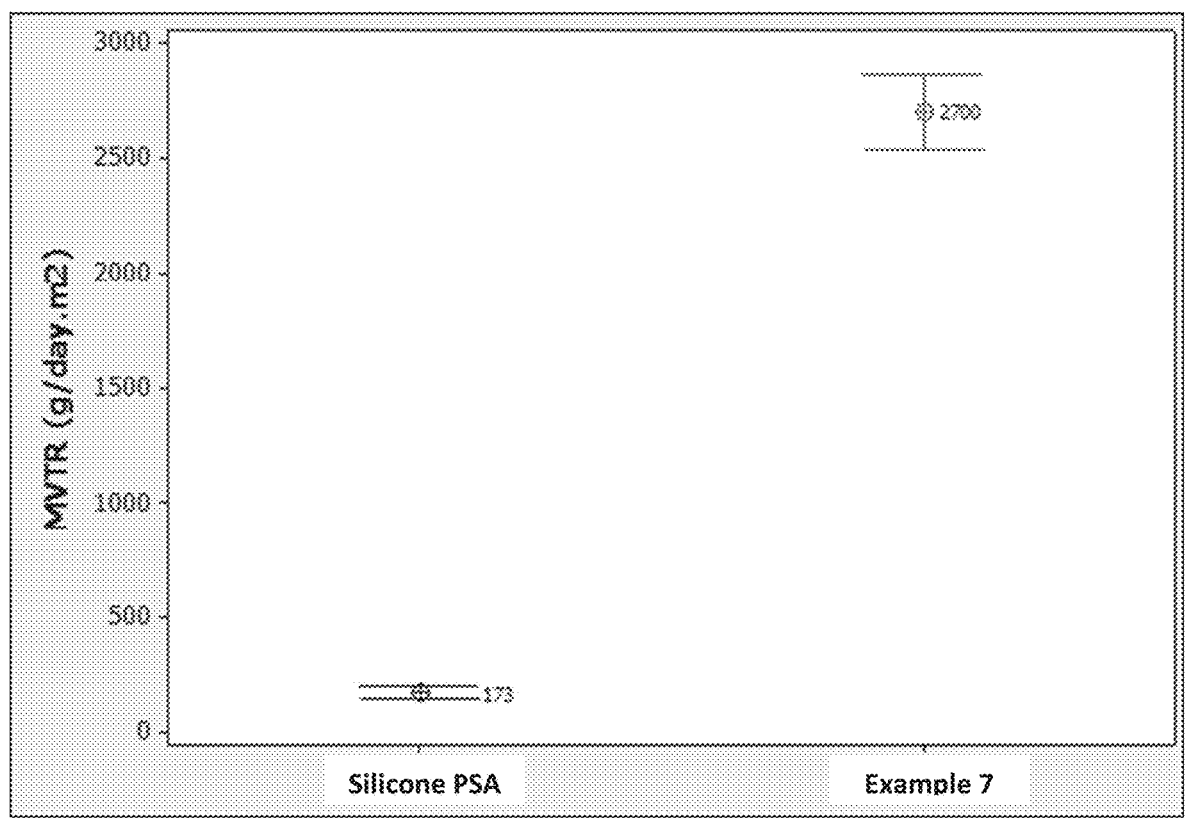
FIG. 13 is a graph of MVTR of MepiTac silicone PSA and Example 7
Figure 14:
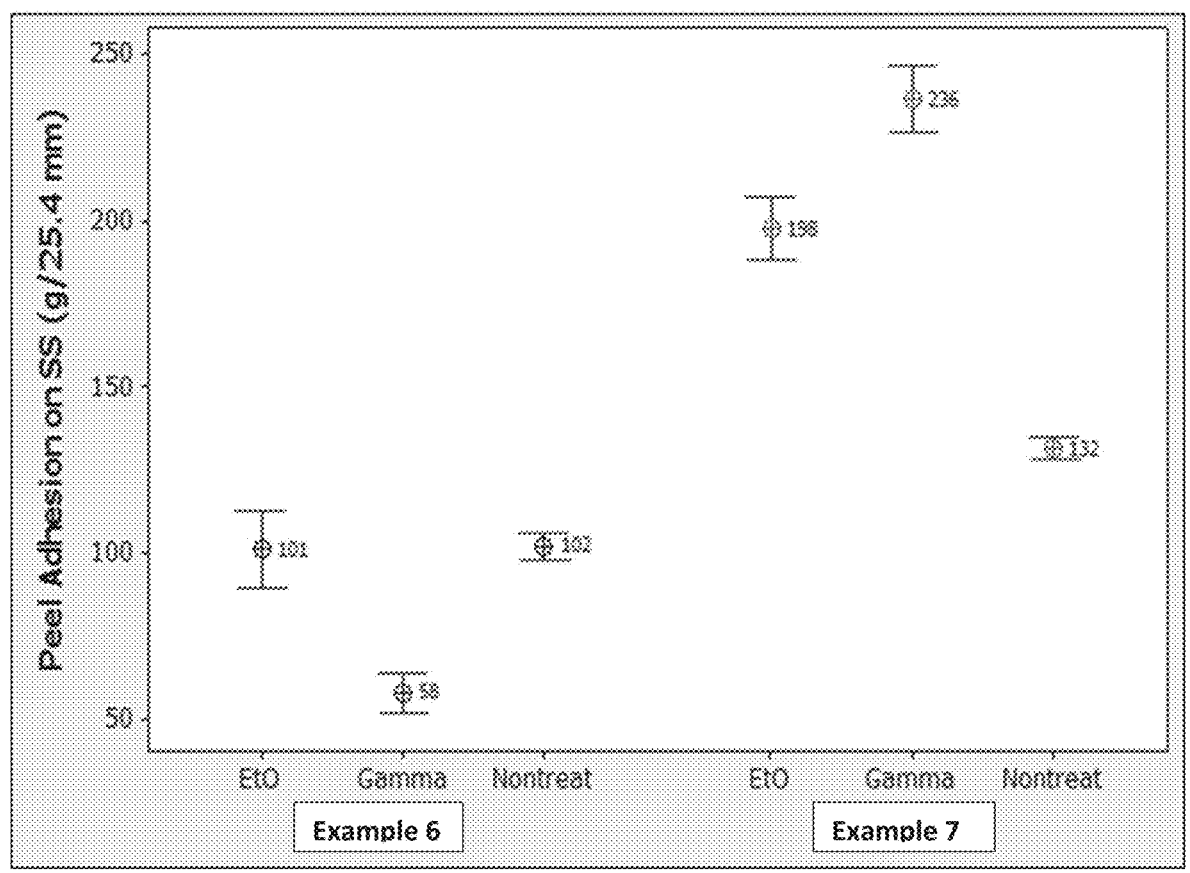
FIG. 14 is a graph of peel adhesion on stainless steel (SS) before and after ethylene oxide (EtO) and Gamma treatment of Example 6 and Example 7.
Figure 15:
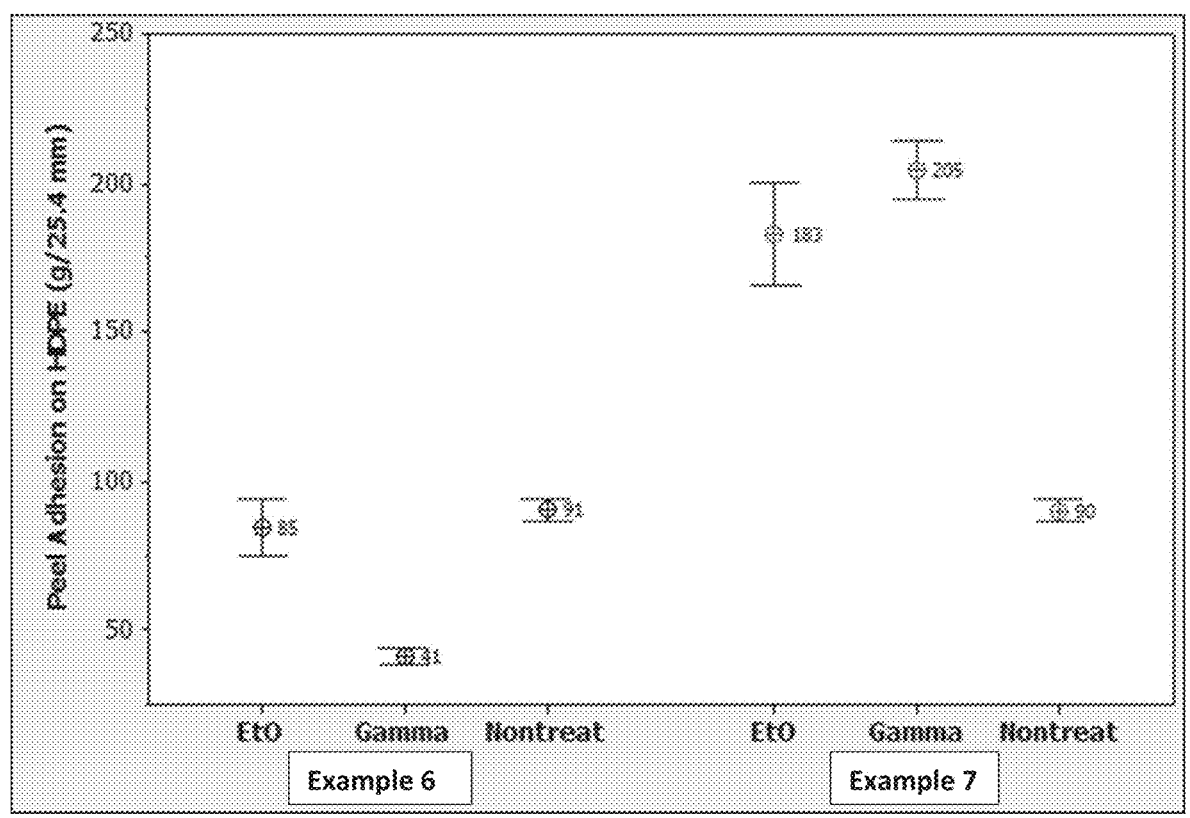
FIG. 15 is a graph of peel adhesion on HDPE before and after ethylene oxide (EtO) and Gamma treatment of Example 6 and Example 7.
Figure 16:
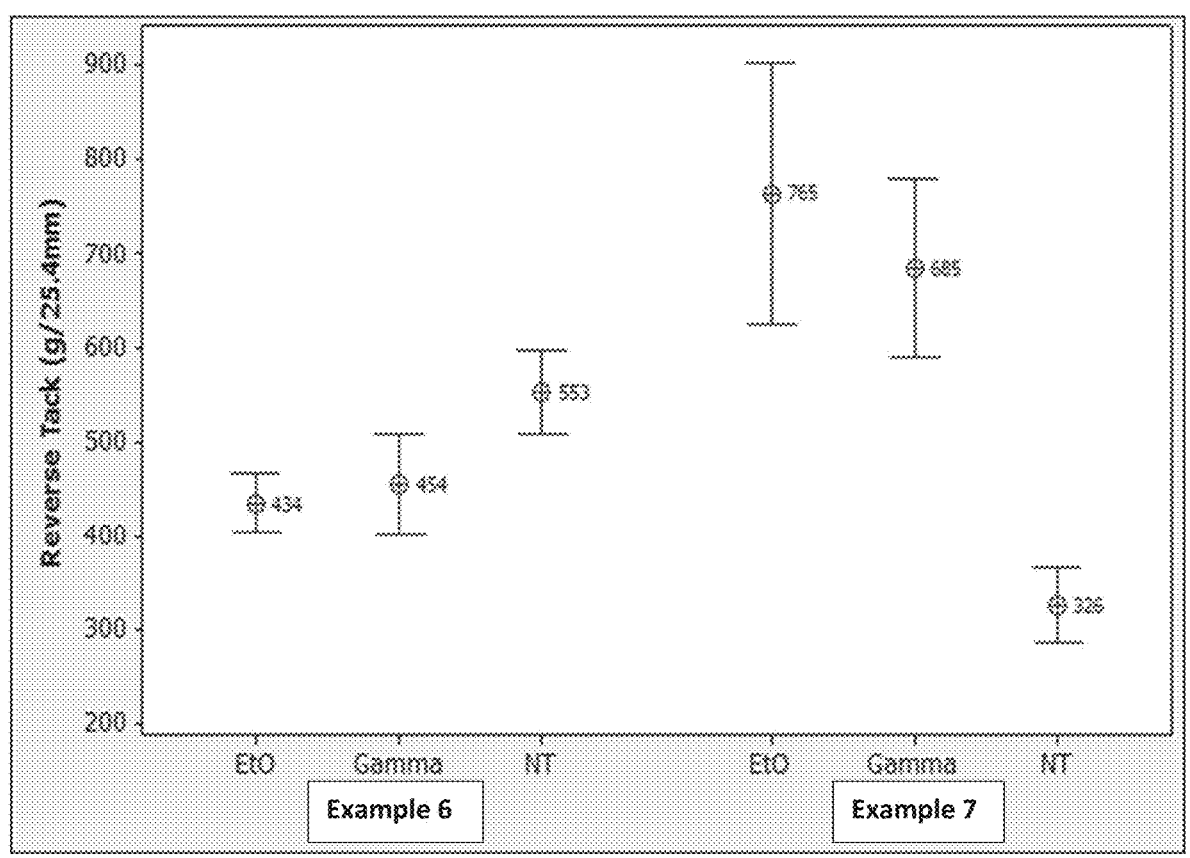
FIG. 16 is a graph of reverse tack before and after ethylene oxide (EtO) and Gamma treatment of Example 6 and Example 7.
Figure 17:
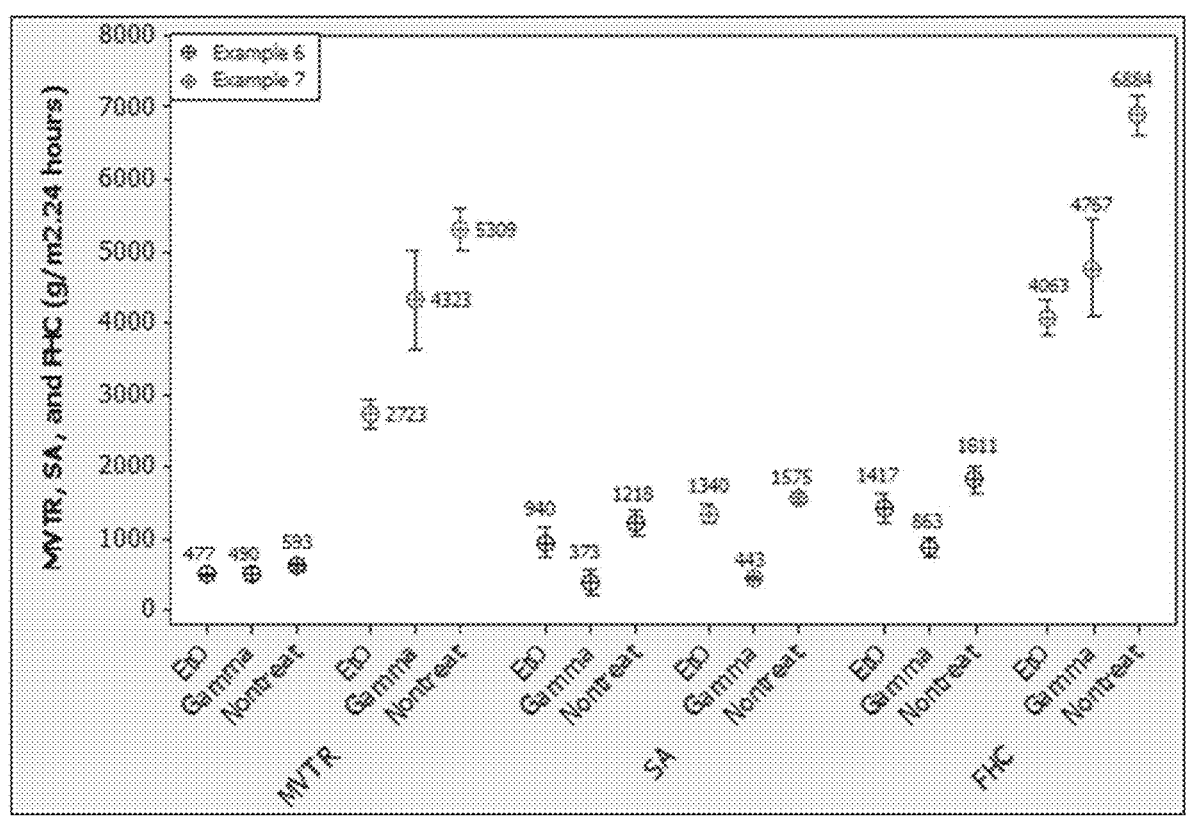
FIG. 17 is a graph of MVTR, SA, and FHC before and after ethylene oxide (EtO) and Gamma treatment of Example 6 and Example 7.

FIGS. 11, 12, and 13 are graphs of peel adhesion on stainless steel and HDPE, reverse tack and MVTR of Example 7 on a 1 mil PU film tape and a commercial silicone gel PSA (Silicone PSA A, which is MepiTac, in these Figures). Both adhesives have similar peel and tack, while Example 7 on a 1 mil PU tape has much higher MVTR (described above), which may be desirable for certain medical applications.

FIGS. 14 to 17 are graphs of peel adhesion on stainless steel and HDPE, reverse tack, MVTR/SA/FHC of Sample 6 and Sample 7 before and after 8 hours of ethylene oxide (EtO) exposure and 25 kGy gamma treatment. EtO and gamma treatment may impact the peel adhesion and moisture handling properties as they with other commercial adhesives.

Figure 18:
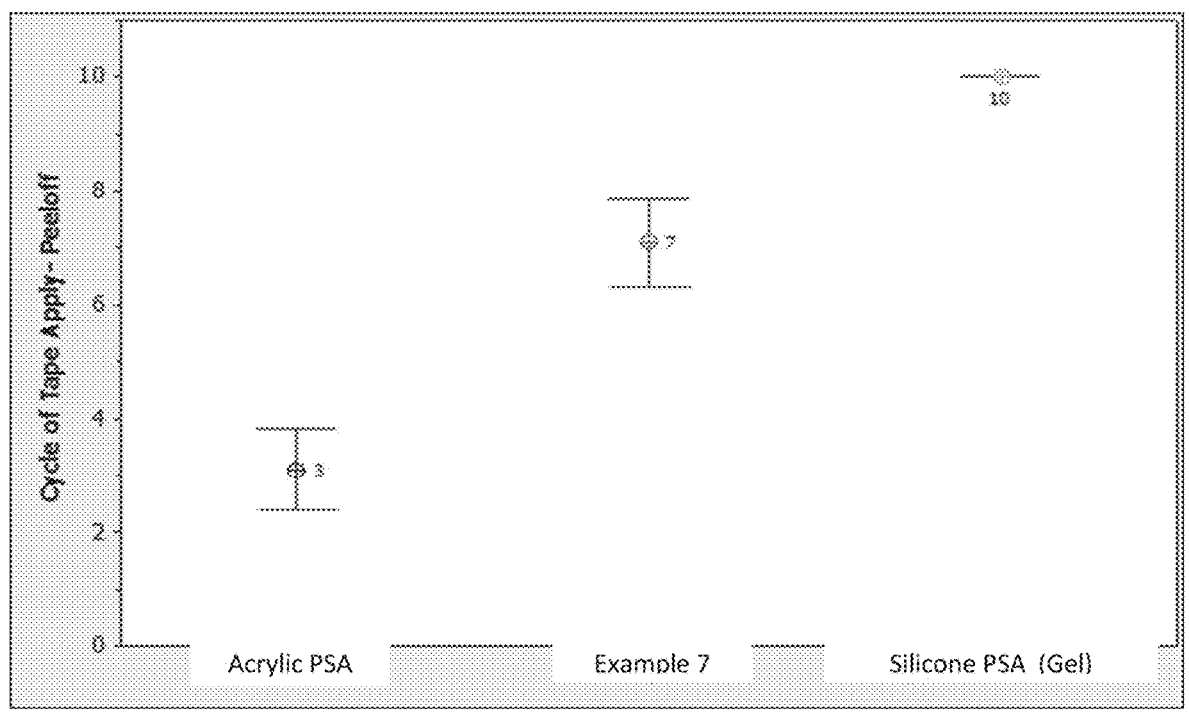
FIG. 18 is a graph of the cycle of tape Apply-Peeloff of an acrylic adhesive, MepiTac silicone gel tape, and Example 7.

FIG. 18 is the graph of the cycle of Apply-Peeloff of Example 7, an acrylic tape and the MepiTac tape on human forearms. Example 7 was able to repositioned approximately 7 times (on average) and performed better than that of many acrylic based medical adhesive tapes and similarly to many silicone gel tapes.

Figure 19:
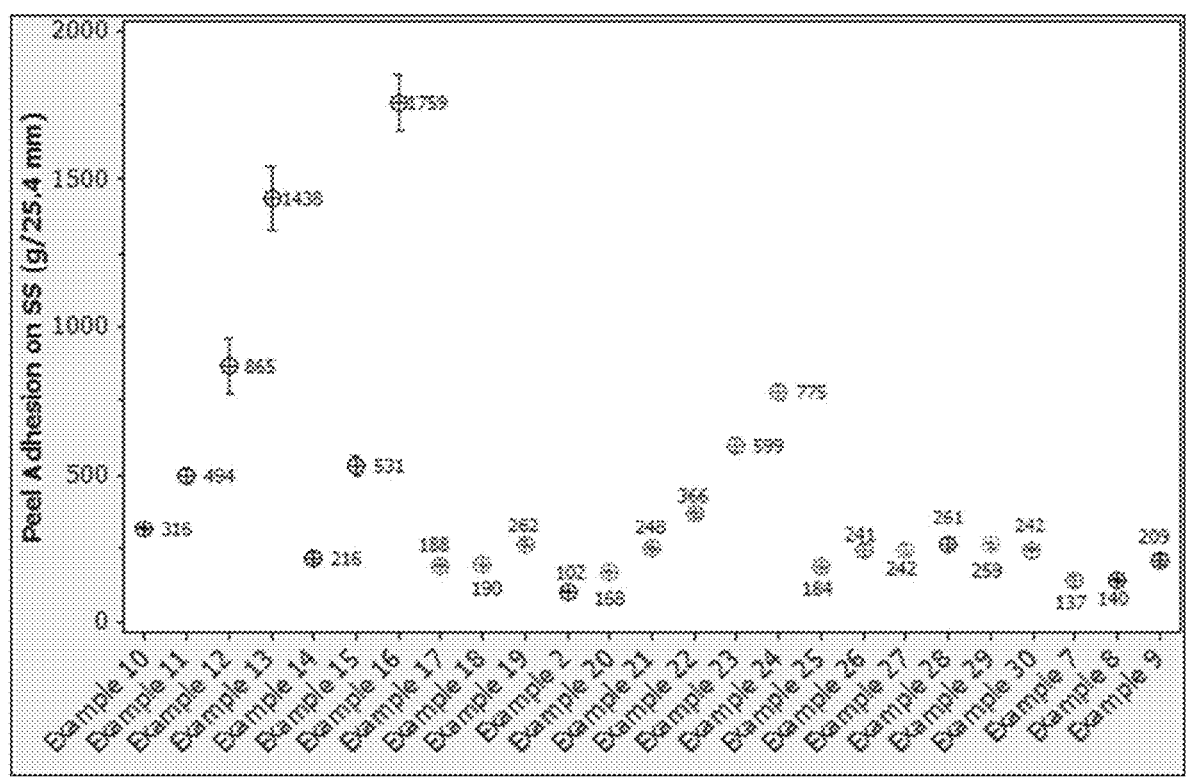
FIG. 19 is a graph of Peel adhesion on Stainless Steel of Examples 7-30.
Figure 20:
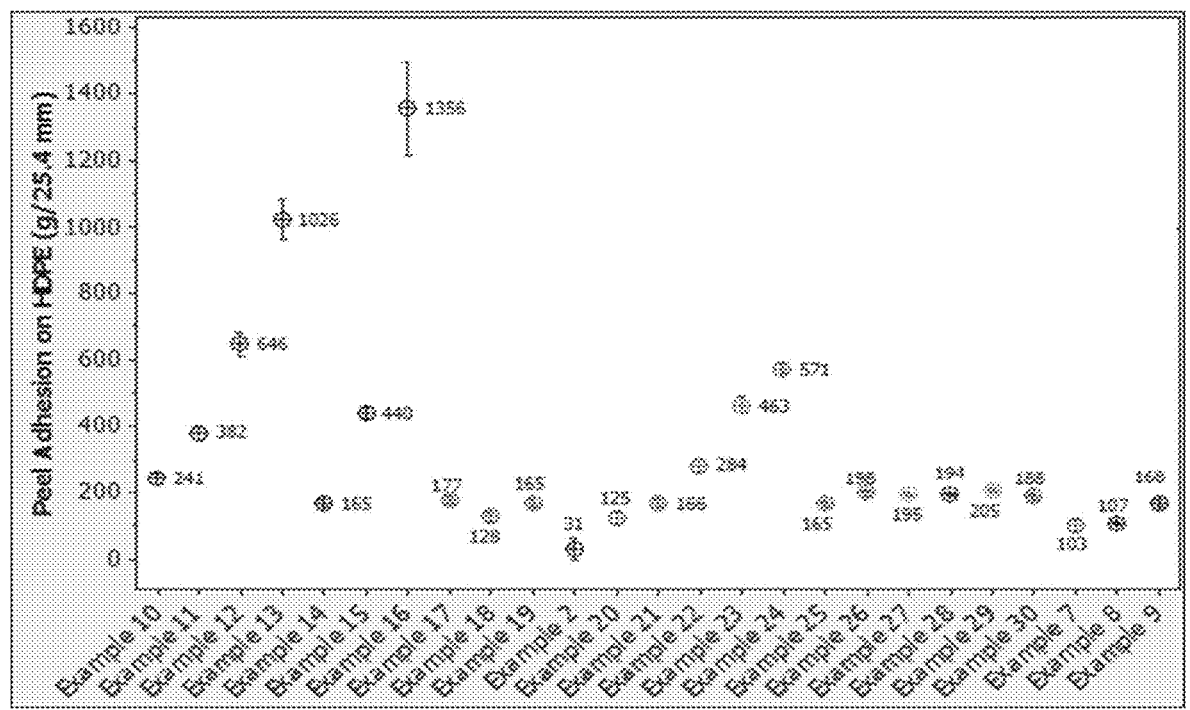
FIG. 20 is a graph of Peel adhesion on HDPE of Examples 7-30.
Figure 21:
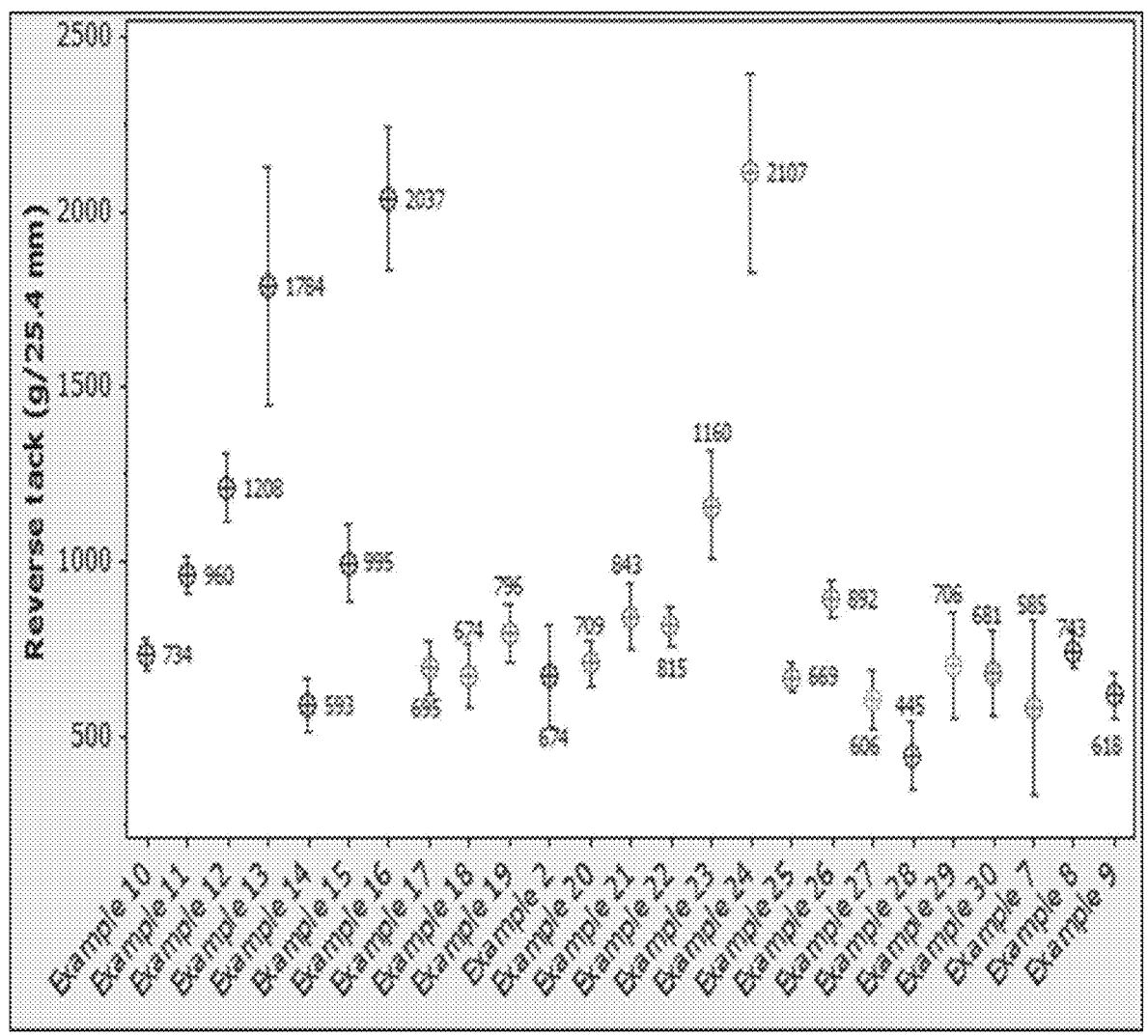
FIG. 21 is a graph of Reverse tack of Examples 7-30.

FIGS. 19 to 21 are graphs of peel adhesion on SS and HDPE and reverse tack of Example 7 to Example 30. These graphs provide that the adhesion and tack of the rubber-based adhesive may be tailored by adjusting the composition of tackifier, oil and rubber and even the loading of different absorbent(s). By changing the tackifier/oil ratio, the adhesion of Example 9 on stainless steel and HDPE may be increased from about 209 g/25.4 mm and about 168 g/25.4 mm to about 1438 g/25.4 mm and about 1026 g/25.4 mm of Example 13 respectively. By further decreasing the rubber loading by about 5%, the adhesion of Example 13 was further increased to about 1759 g/25.4 mm and about 1356 g/25.4 mm of Example 16. As also shown in FIGS. 19 to 21, at least one absorbent (such as A800 and Avicel PH 105) may decrease the adhesion but may not affect the tack of the adhesive. The wide variety of options in adhesion properties allow the rubber-based adhesives described herein to be adjusted for different medical applications with different requirements.

Figure 22:
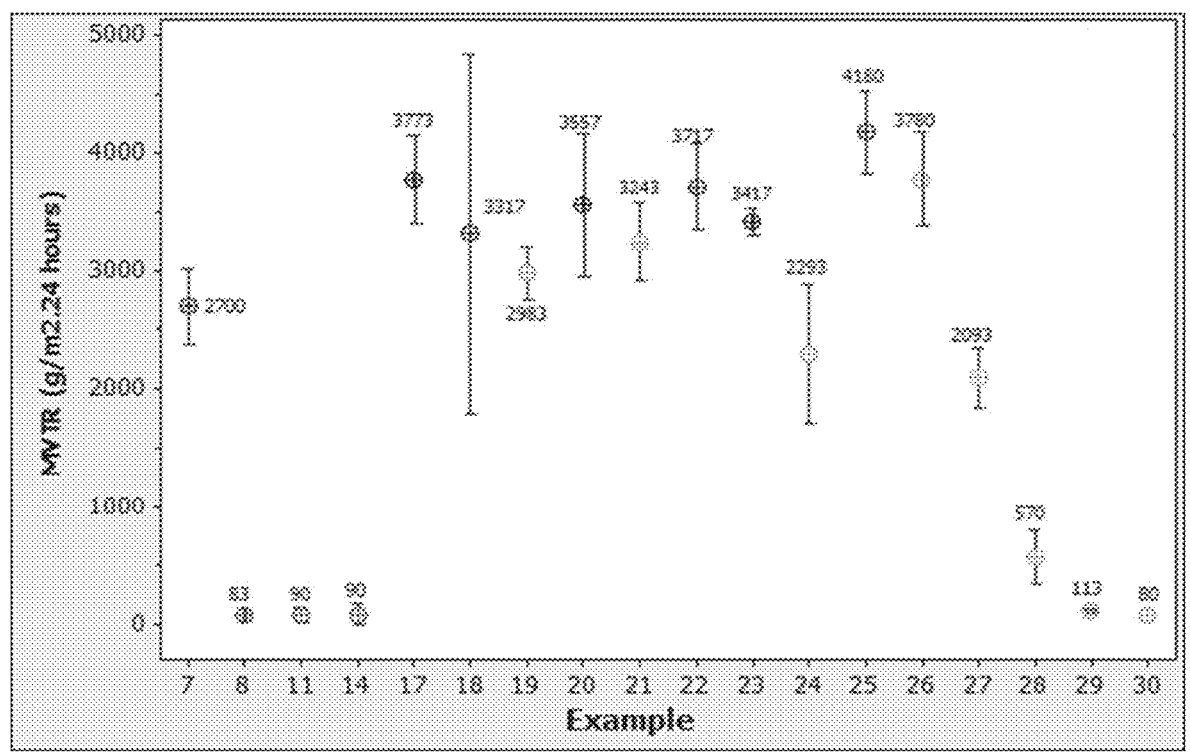
FIG. 22 is a graph of MVTR of Examples 7, 8, 11, 14, and 17-30.
Figure 23:
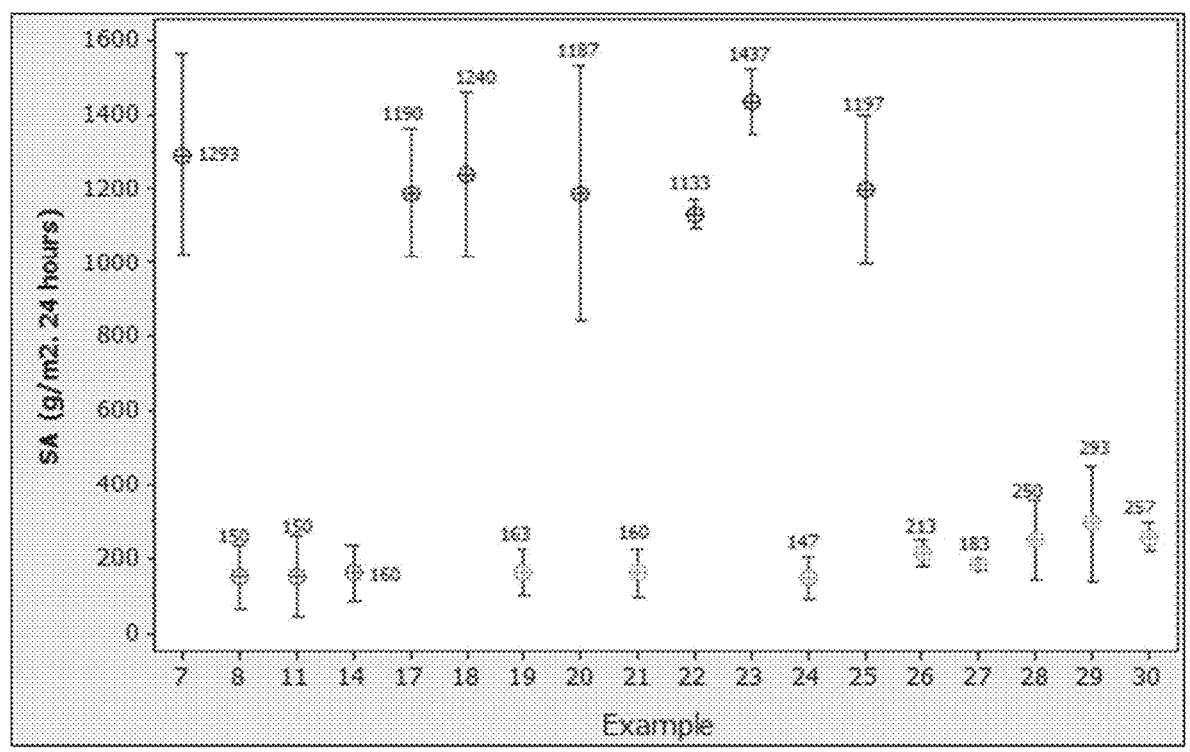
FIG. 23 is a graph of SA of Examples 7, 8, 11, 14, and 17-30.

FIG. 22 and FIG. 23 are graphs of MVTR and SA of Examples 7, 8, 11, and 17-30. Compared rubber adhesives without absorbent(s), Examples 8, 11, and 14, the absorbents (both A800 and Avicel PH 105 in this example) may increase the moisture handling capacity, up to about 4180 g/m². 24 hours and about 1437 g/m². 24 hours for MVTR and SA respectively. MVTR of Examples 21 and 27-30 also show that there may be a threshold of absorbent loading to form a path for moisture in order to get high MVTR. For certain absorbents (such as Avecil PH 105), high MVTR may be achieved when the loading was at least about 20% (see Example 27 where MVTR is greater than about 500 g/m². 24 hours). Further, as shown in FIG. 23, by selecting at least one absorbent (such as Avecil PH105) which do not absorb moisture or water itself, rubber adhesives can only conduct moisture. Where the absorbent does not absorb moisture or water itself, the adhesive tape may not swell while still providing a high MVTR to conduct moisture away. On the other hand, an adhesive tape itself which absorbs moisture or water and has high MVTR can be designed by selecting certain absorbent(s) (such as A800). The wide variety of options in fluid handling capacity may allow for providing medical applications with different MVTR and other requirements.

Figure 24:
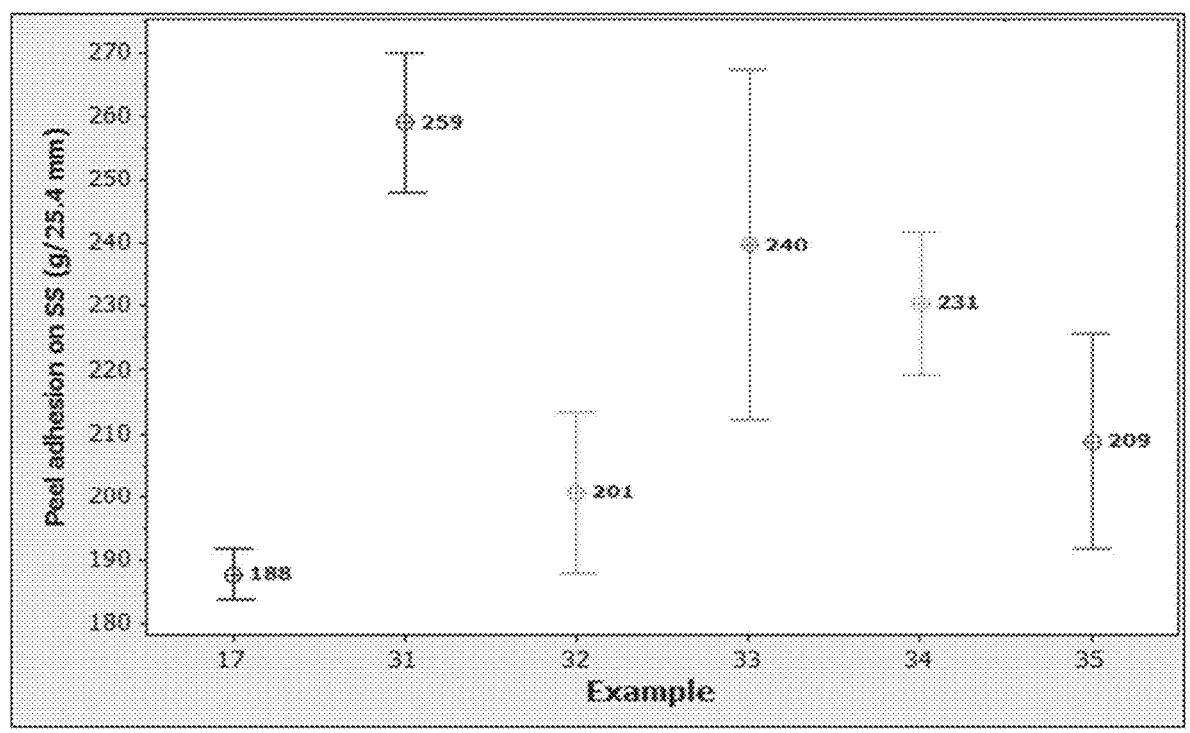
FIG. 24 is a graph of Peel adhesion on stainless steel of Example 17 and Examples 31-35.
Figure 25:
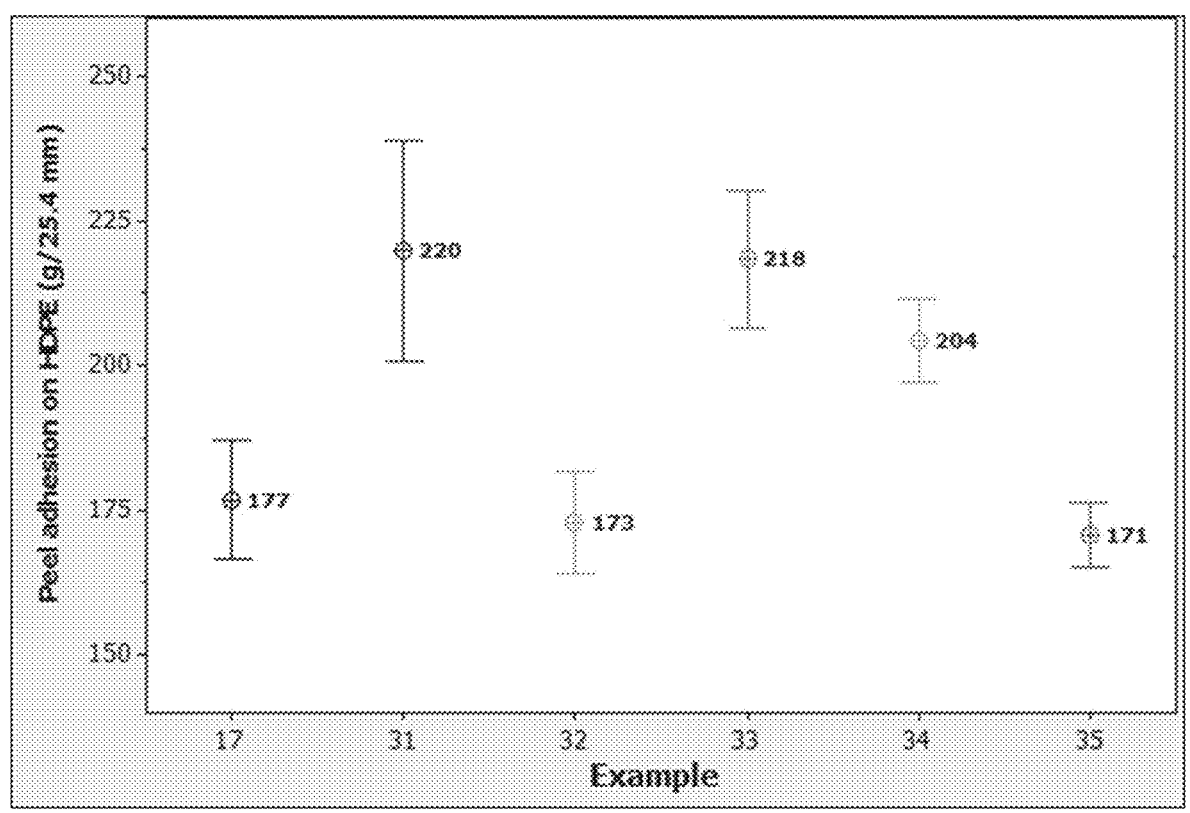
FIG. 25 is a graph of Peel adhesion on HDPE of Example 17 and Examples 31-35.
Figure 26:
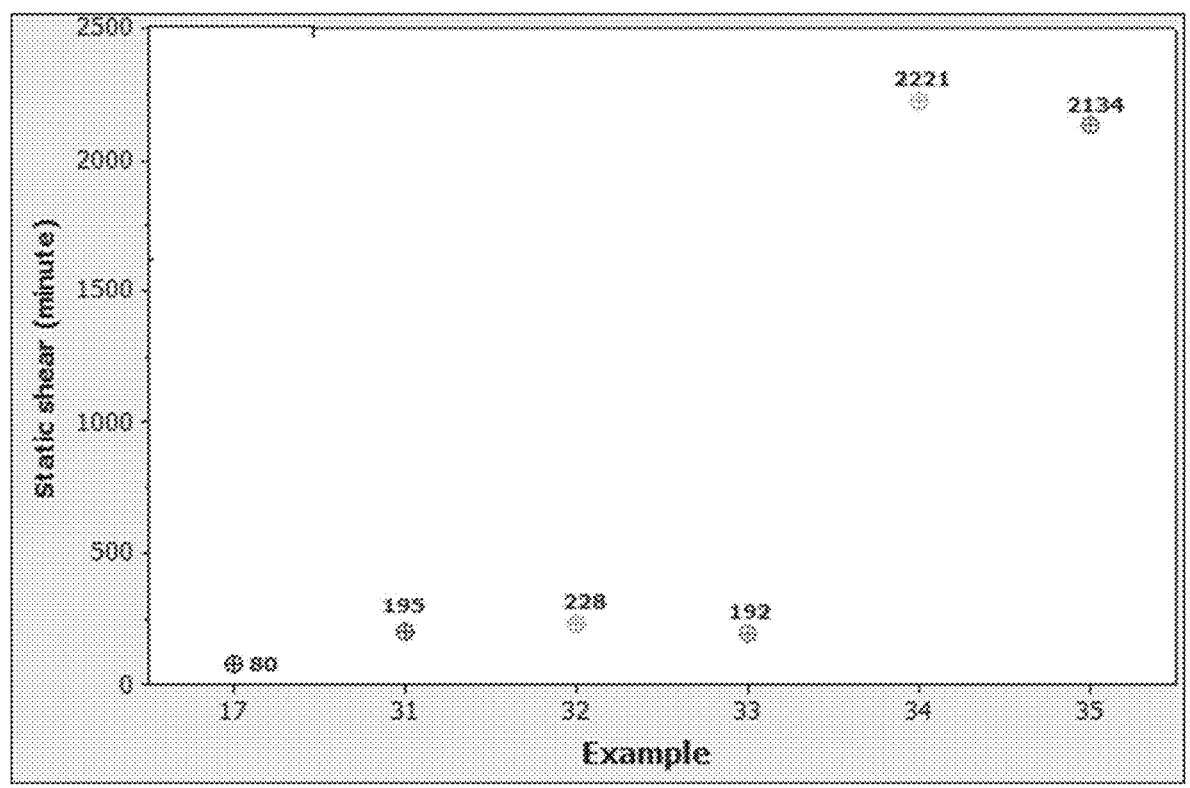
FIG. 26 is a graph of Reverse tack of Example 17 and Examples 31-35.

FIGS. 24 to 26 are graphs of peel adhesion and static shear of Example 17 and Examples 31-35. With the introduction of about 5% of short fibers (about 1 mm to about 15 mm long) such as PET, PVA, PP, viscose and fibrillated PE to Example 17, the static shear and the integrity may be increased without decreasing the adhesion of the adhesive.

The present subject matter includes all operable combinations of features and aspects described herein. Thus, for example if one feature is described in association with an embodiment and another feature is described in association with another embodiment, it will be understood that the present subject matter includes embodiments having a combination of these features. Many other benefits will no doubt become apparent from future application and development of this technology.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A rubber-based skin adhesive consisting of:
from about 7% to about 33% of at least one rubber component selected from the group consisting of a linear or radial A-B-A block copolymer, linear or radial A-B block copolymer, branched block copolymer, olefinic block copolymer and combinations thereof;
from about 15% 45% of at least one tackifier selected from the group consisting of a hydrogenated pentaerythritol rosin ester, a hydrogenated hydrocarbon resin, a styrenated terpene resin, and combinations thereof;
from about 15% about 60% of at least one mineral oil; and
from about 30% to about 40% of at least one absorbent;
at least one additive selected from the group consisting of a natural clay, a synthetic clay, a micro fibers, nano fibers, fibrils of fibers, an antioxidant, a stabilizer, and combinations thereof;
optionally, at least one active ingredient;
wherein the adhesive exhibits a soft, gel-like consistency and is repositionable on skin; and
wherein the ratio of the amount of the tackifier to the amount of the rubber component ranges from 1:1 to 2.4:1; and
wherein the ratio of the amount of the oil to the amount of the rubber component ranges from 1.3:1 to 2.6:1.

2. The adhesive of claim 1 wherein at least one absorbent comprises carboxymethyl cellulose.

3. The adhesive of claim 1 wherein at least one active ingredient is chlorhexidine gluconate (CHG).

4. The adhesive of claim 1 wherein at least one mineral oil is a USP White Mineral Oil.

5. The adhesive of claim 1 wherein at least one oil includes a liquid polymer selected from the group comprising liquid isoprene rubber, liquid butadiene rubber, liquid polyisobutylene (PIB), and combinations thereof.

6. The adhesive of claim 1 wherein the adhesive exhibits a storage modulus (G') at a temperature of about 22° C. to about 37° C. and a frequency of about 0.01 rad/s of about 100 Pa to about 30,000 Pa.

7. The adhesive of claim 1 wherein the adhesive exhibits a storage modulus (G') at a temperature of about 22° C. to about 37° C. and a frequency of about 100 rad/s of about 5,000 Pa to about 150,000 Pa.

8. The adhesive of claim 1 wherein the adhesive exhibits a loss modulus (G") at a temperature of about 22° C. to about 37° C. and a frequency of about 0.01 rad/s of about 100 Pa to about 10,000 Pa.

9. The adhesive of claim 1 wherein the adhesive exhibits a loss modulus (G") at a temperature of about 22° C. to about 37° C. and a frequency of about 100 rad/s of about 1,000 Pa to about 30,000 Pa.

10. The adhesive of claim 1 wherein the adhesive has a glass transition temperature within a range from about −70° C. to about 0° C.

* * * * *